United States Patent
Margallo Balbás et al.

(10) Patent No.: US 10,835,313 B2
(45) Date of Patent: Nov. 17, 2020

(54) RADIOFREQUENCY ABLATION CATHETER WITH OPTICAL TISSUE EVALUATION

(71) Applicant: MEDLUMICS S.L., Tres Cantos-Madrid (ES)

(72) Inventors: Eduardo Margallo Balbás, Madrid (ES); José Luis Rubio Guivernau, Madrid (ES); Santiago Jiménez Valero, Madrid (ES); Alejandro Barriga Rivera, Seville (ES); Justo Contreras Bermejo, Madrid (ES); Juan Lloret Soler, Madrid (ES)

(73) Assignee: MEDLUMICS S.L., Madrid (ES)

( * ) Notice: Subject to any disclaimer, the term of this patent is extended or adjusted under 35 U.S.C. 154(b) by 0 days.

(21) Appl. No.: 14/608,026

(22) Filed: Jan. 28, 2015

(65) Prior Publication Data

US 2015/0209105 A1    Jul. 30, 2015

Related U.S. Application Data

(60) Provisional application No. 61/933,752, filed on Jan. 30, 2014.

(51) Int. Cl.
*A61B 18/14*    (2006.01)
*A61B 5/00*    (2006.01)
(Continued)

(52) U.S. Cl.
CPC ........ *A61B 18/1492* (2013.01); *A61B 5/0036* (2018.08); *A61B 5/0066* (2013.01);
(Continued)

(58) Field of Classification Search
None
See application file for complete search history.

(56) References Cited

U.S. PATENT DOCUMENTS 531,501 A    12/1894    Bishop
4,960,134 A    10/1990    Webster, Jr.
(Continued)

FOREIGN PATENT DOCUMENTS

CN    1867299 A    11/2006
CN    102209497 A    10/2011
(Continued)

OTHER PUBLICATIONS

Jacques, S. L. and S. A. Prahl, Modeling optical and thermal distributions in tissue during laser irradiation. Lasers Surg Med, 1987. 6(6): p. 494-503. [0152].*
(Continued)

*Primary Examiner* — Erica S Lee
(74) *Attorney, Agent, or Firm* — Sterne, Kessler, Goldstein & Fox P.L.L.C.

(57) ABSTRACT

Systems and methods for performing RF ablation while monitoring the procedure using low coherence interferometry (LCI) data are described. A catheter includes a distal section, a proximal section, a multiplexer, and a sheath coupled between the distal section and the proximal section. The distal section includes one or more electrodes configured to apply RF energy to a portion of a sample in contact with the electrode. The distal section also includes a plurality of optical elements configured to transmit one or more beams of exposure radiation away from the distal section of the catheter. The proximal section includes an optical source configured to generate a source beam of radiation and a detector configured to generate depth-resolved optical data. The multiplexer is configured to generate the one or more beams of exposure radiation from the source beam of radiation.

12 Claims, 11 Drawing Sheets

(51) Int. Cl.
*A61B 5/053* (2006.01)
*A61B 18/24* (2006.01)
*A61B 18/00* (2006.01)
*A61B 5/01* (2006.01)
*A61B 17/00* (2006.01)
*A61B 34/10* (2016.01)
*A61B 90/00* (2016.01)

(52) U.S. Cl.
CPC .......... *A61B 5/0084* (2013.01); *A61B 5/0538* (2013.01); *A61B 5/4836* (2013.01); *A61B 5/4848* (2013.01); *A61B 5/6852* (2013.01); *A61B 5/6885* (2013.01); *A61B 5/6886* (2013.01); *A61B 18/24* (2013.01); *A61B 5/01* (2013.01); *A61B 5/742* (2013.01); *A61B 2017/00057* (2013.01); *A61B 2018/00351* (2013.01); *A61B 2018/00357* (2013.01); *A61B 2018/00577* (2013.01); *A61B 2018/00636* (2013.01); *A61B 2018/00785* (2013.01); *A61B 2018/00791* (2013.01); *A61B 2018/00875* (2013.01); *A61B 2018/00916* (2013.01); *A61B 2018/00982* (2013.01); *A61B 2034/104* (2016.02); *A61B 2090/064* (2016.02); *A61B 2505/05* (2013.01); *A61B 2562/0242* (2013.01); *A61B 2576/023* (2013.01)

(56) References Cited

U.S. PATENT DOCUMENTS

| | | | |
|---|---|---|---|
| 5,459,570 | A | 10/1995 | Swanson et al. |
| 6,123,702 | A | 9/2000 | Swanson et al. |
| 6,228,076 | B1 | 5/2001 | Winston et al. |
| 6,283,921 | B1 | 9/2001 | Nix et al. |
| 6,384,915 | B1* | 5/2002 | Everett ............... A61B 5/0066 356/336 |
| 7,291,146 | B2 | 11/2007 | Steinke et al. |
| 7,527,625 | B2 | 5/2009 | Knight et al. |
| 7,662,152 | B2* | 2/2010 | Sharareh ............ A61B 18/1492 606/15 |
| 8,663,083 | B2 | 3/2014 | Georgi et al. |
| 9,062,960 | B2 | 6/2015 | Rubio Guivernau et al. |
| 2002/0087156 | A1 | 7/2002 | Maguire et al. |
| 2005/0222558 | A1 | 10/2005 | Baxter et al. |
| 2006/0122587 | A1 | 6/2006 | Sharareh |
| 2006/0184043 | A1 | 8/2006 | Tromberg et al. |
| 2007/0066983 | A1 | 3/2007 | Maschke |
| 2007/0270792 | A1 | 11/2007 | Hennemann et al. |
| 2007/0282403 | A1 | 12/2007 | Tearney et al. |
| 2007/0287998 | A1 | 12/2007 | Sharareh et al. |
| 2009/0005768 | A1* | 1/2009 | Sharareh ............ A61B 18/1492 606/17 |
| 2009/0131931 | A1 | 5/2009 | Lee et al. |
| 2009/0287092 | A1* | 11/2009 | Leo .................... A61B 5/00 600/474 |
| 2010/0076299 | A1 | 3/2010 | Gustus et al. |
| 2010/0196624 | A1* | 8/2010 | Ruuttu ................ B23K 26/067 427/569 |
| 2011/0028837 | A1* | 2/2011 | Byrd .................... A61B 5/0071 600/433 |
| 2011/0028967 | A1* | 2/2011 | Rollins ................ A61B 5/0066 606/41 |
| 2011/0029049 | A1* | 2/2011 | Vertikov ............. A61B 5/14532 607/104 |
| 2011/0172659 | A1 | 7/2011 | Brannan |
| 2011/0257641 | A1 | 10/2011 | Hastings et al. |
| 2012/0105812 | A1 | 5/2012 | Dekker et al. |
| 2012/0265184 | A1 | 10/2012 | Sliwa et al. |
| 2013/0201485 | A1* | 8/2013 | Rubio-Guivernau ........................ G01B 9/02091 356/479 |
| 2013/0253330 | A1 | 9/2013 | Demos |
| 2014/0078510 | A1 | 3/2014 | Rubio Guivernau et al. |
| 2014/0094792 | A1* | 4/2014 | Sharonov ............... G01K 11/12 606/34 |
| 2014/0118748 | A1 | 5/2014 | Rubio Guivernau et al. |
| 2014/0121659 | A1* | 5/2014 | Paul .................... A61B 18/1492 606/34 |
| 2014/0276690 | A1* | 9/2014 | Grace .................. A61B 18/24 606/12 |

FOREIGN PATENT DOCUMENTS

| | | |
|---|---|---|
| EP | 1922991 | 5/2008 |
| EP | 2062545 | 5/2009 |
| EP | 2550924 | 1/2013 |
| ES | 2396391 | 2/2013 |
| ES | 2415555 | 7/2013 |
| JP | H06-511312 A | 12/1994 |
| JP | H07-079995 A | 3/1995 |
| JP | 2008520364 A | 6/2008 |
| JP | 2009148550 A | 7/2009 |
| JP | 2010-511467 A | 4/2010 |
| JP | 2011-143252 A | 7/2011 |
| JP | 2007-083054 A | 8/2012 |
| JP | 2015506483 A | 3/2015 |
| WO | WO 2000013574 A1 | 3/2000 |
| WO | WO 2003/088817 A2 | 10/2003 |
| WO | WO 2007/149603 | 12/2007 |
| WO | WO 2010/082146 | 7/2010 |
| WO | WO 2013/043402 | 3/2013 |

OTHER PUBLICATIONS

International Search Report and Written Opinion of the International Searching Authority directed to related European Application No. PCT/EP2015/051916, dated Apr. 21, 2015; 14 pages.

Wright et al., Denaturation of Collagen via Heating: An Irreversible Rate Process, Annual Review of Biomedical Engineering, 2002: 4: 109-128.

Pierce MC et al., Collagen denaturation can be quantified in burned human skin using polarization-sensitive optical coherence tomography, Burns, 2004; 30: 511-517.

Wood et al., Navigation Systems for Ablation, J Vas Interv Radiol, 2010; 21:S257-S263.

Reddy et al., The relationship between contact force and clinical outcome during radiofrequency catheter ablation of atrial fibrillation in the TOCCATA study. Heart Rhythm, 2012; 9:1789-95.

Nakagawa et al., Locations of High Contact Force During Left Atrial Mapping in Atrial Fibrillation Patients: Electrogram Amplitude and Impedance are Poor Predictors of Electrode-Tissue Contact Force for Ablation of Atrial Fibrillation, Circulation Arrhythmia and Electrophysiology, 2013; 7 pages.

Kumar et al., Predictive valuve of impedance changes for real-time contact force measurements during catheter ablation of atrial arrhythmias in humans, Heart Rhythm, 2013; 10:962-9.

Petersen et al., Temperature-Controlled Radiofrequency Ablation of Cardiac Tissue: an in Vitro Study of the Impact of Electrode Orientation, Electrode Tissue Contact Pressure and External Convective Cooling, Journal of Interventional Cardiac Electrophysiology, Oct. 1999; 3(3):257-62.

Petersen et al., Lesion Dimensions During Temperature-Controlled Radiofrequency Catheter Ablation of Left Ventricular Porcine Myocardium: Impact of Ablation Site, Electrode Size, and Convective Cooling, Circulation, Jan. 19, 1999;99(2):319-25.

Mu et al., Temperature Induced Denaturation of Collagen in Acidic Solution, Biopolymers, 2007; 86: 282-287.

Foppen, Experimental and Numerical Analysis of Lesion Growth during Cardiac Radiofrequency Ablation, Apr. 2009; 51 pages.

Fleming et al., In vitro characterization of cardiac radiofrequency ablation lesions using optical coherence tomography, Opt. Express, 2010; 18:3079-3092.

Faber, Functional Optical Coherence Tomography: spatially resolved measurements of optical properties, PhD Thesis, 2005; 116 pages.

(56) References Cited

OTHER PUBLICATIONS

Camm et al., "Guidelines for the Management of Atrial Fibrillation," European Heart Journal, 2010, vol. 31, No. 19; pp. 2369-2429.
D'Silva et al., "Advances in Imaging for Atrial Fibrillation Ablation," Radiology Research and Practice, Feb. 16, 2011; 15 pages.
Langberg et al., "Temperature Monitoring During Radiofrequency Catheter Ablation of Accessory Pathways," Circulation, The American Heart Association, Nov. 1992, 7 pages, vol. 86, issue 5; 7 pages.
Marchlinski et al., "Linear Ablation Lesions for Control of Unmappable Ventricular Tachycardia in Patients With Ischemic and Nonischemic Cardiomyopathy," Circulation, American Heart Association, Mar. 21, 2000, vol. 101, issue 11; pp. 1288-1296.
Perna et al., "Assessment of catheter tip contact force resulting in cardiac perforation in swine atria using force sensing technology," Circulation Arrhythm Electrophysiol, American Heart Association, Jan. 19, 2011, vol. 4; pp. 218-224.
Ames et al., "Catheter Ablation of Atrial Fibrillation," Cardiology Patient Page, American Heart Association, 2006; 4 pages.
Klein et al., "Radiofrequency catheter ablation of ventricular tachycardia in patients without structural heart disease," Circulation, American Heart Association, May 1, 1992, vol. 85, issue 5; pp. 1666-1674.
Wood, M., "Exposing gaps in linear radiofrequency lesions: form before function," Circulation Arrhythm Electrophysiol, 2011, vol. 4; pp. 257-259.
Wang et al., "In vivo intracardiac optical coherence tomography imaging through percutaneous access: toward image-guided radiofrequency ablation," Journal of Biomedical Optics, Nov. 2011, vol. 16, No. 11; 2 pages.
Wright et al., "Real-time lesion assessment using a novel combined ultrasound and radiofrequency ablation catheter," Heart Rhythm, Feb. 2011, vol. 8; pp. 302-312.
Adler et al., "Three-dimensional optical coherence tomography of Barrett's esophagus and buried glands beneath neo-squamous epithelium following radiofrequency ablation," Endoscopy, 2010, vol. 41, No. 9; pp. 773-776.
Fu et al., "Fiber-optic catheter-based polarization-sensitive OCT for radio-frequency ablation monitoring," Optical Letter, Sep. 1, 2014, vol. 37, No. 17; 12 pages.
Hitzenberger et al., "Measurement and imaging of birefringence and optic axis orientation by phase resolved polarization sensitive optical coherence tomography," Optics Express, 2001, vol. 9, No. 13; 11 pages
Guerra et al., "Effects of open-irrigated radiofrequency ablation catheter design on lesion formation and complications: in vitro comparison of 6 different devices," Journal of Cardiovascular Electrophysiology, 2013, vol. 24, No. 10; pp. 1157-1162.
Nakagawa et al., "Inverse relationship between electrode size and lesion size during radiofrequency ablation with active electrode cooling," Circulation, Aug. 1998, vol. 98, issue 5; pp. 458-465.
Oron et al., "The influence of radiofrequency ablation patterns on length, histological and mechanical properties of tendons," Muscles, Ligaments and Tendons Journal, 2012, vol. 2, No. 2; pp. 85-90.
International Preliminary Report on Patentability directed to related European Application No. PCT/EP2015/051916, completed Mar. 3, 2016; 31 pages.
Nardella P. C., "Radio frequency energy and impedance feedback," SPIE, 1989, vol. 1068; 9 pages.
Todorovic et al., "In vivo burn imaging using Mueller optical coherence tomography," Optics Express, 2008, vol. 16, No. 14; pp. 10279-10284.
Neet et al., "Optical coherence reflectometry (OCR) guided RF ablation guide wire for total occlusions," SPIE, 2001, vol. 4244; 9 pages.
Search Report in related Japanese Patent Application No. 2017506943, dated Nov. 26, 2018, with attached English-language translation; 45 pages.
Written Opinion in related Japanese Patent Application No. 2017506943, dated Mar. 4, 2019, with attached English-language translation; 15 pages.

\* cited by examiner

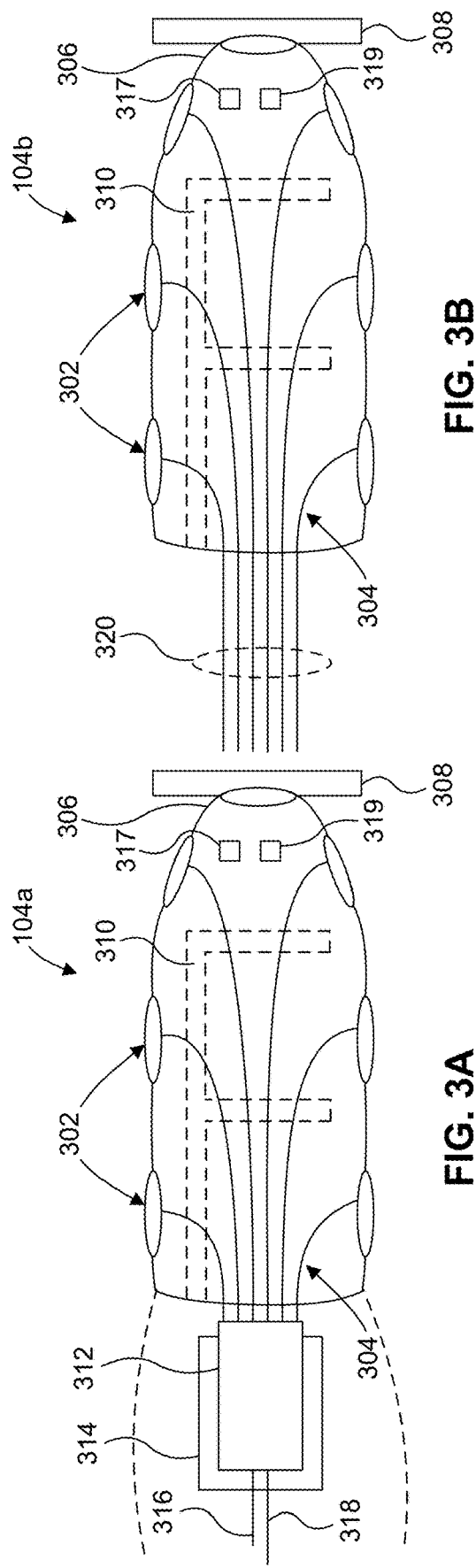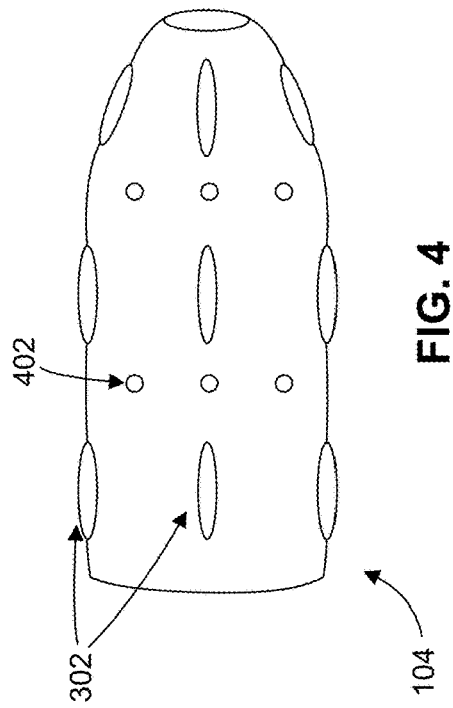

RADIOFREQUENCY ABLATION CATHETER WITH OPTICAL TISSUE EVALUATION

CROSS-REFERENCE TO RELATED APPLICATIONS

This application claims the benefit under 35 U.S.C. § 119(e) of U.S. provisional patent application Ser. No. 61/933,752, filed Jan. 30, 2014, which is incorporated by reference herein in its entirety.

BACKGROUND

Field

Embodiments of the invention relate to designs of, and methods of using, an RF ablation catheter together with optical tissue inspection.

Background

Radiofrequency (RF) ablation is a medical technique to produce tissue necrosis. It is used to help treat different pathologies including cancer, Barret's esophagus, or cardiac arrhythmias, among others. The application of alternating current with an oscillating frequency above several hundreds of kHz avoids the stimulation of excitable tissue while delivering heat by means of the Joule's effect. The increase in tissue temperature produces denaturation of the biological molecules, including proteins such as collagen. Traditionally, RF ablation is done by placing an external electrode on the patient's body, and applying an alternating potential to the tip of a catheter that is placed in contact with the tissue to be treated within the patient's body. The ablation effect depends on a number of factors, including applied electrical power, quality of the electrical contact, local tissue properties, presence of blood flow close to the tissue surface, and the effect of irrigation. Because of the variability of these parameters, it is difficult to obtain consistent results.

Indeed, this procedure has shown only limited effectiveness when used in atrial fibrillation, with individual success rates strongly dependent on the expertise and ability of the clinician performing it. Even in qualified centers, in the acute phase after ablation, successful treatment rates only go up to 80%, while recurrences in a year follow-up period may reach 20%. Some factors associated to recurrent cases are discontinuous ablation lines and incomplete wall ablation. Incomplete ablation resulting in edema rather than complete necrosis cannot be properly identified with current tools.

One further problem with catheter ablation is the long intervention times that are required in point-to-point procedures in the atrium. In these cases, continuous lines are created in a pre-defined pattern around anatomical structures to obtain the desired electrical isolation effect. Since ablation is done locally, a large number of individual lesions are commonly concatenated. Ensuring the continuity of such a pattern in a beating heart requires painstaking work and attention. Since the procedure is often performed with the support of fluoroscopy, it can pose a significant radiation dose to the clinician and the patient.

BRIEF SUMMARY

The usage of point-to-point RF ablation to help mitigate the effects of atrial fibrillation are improved by providing direct and immediate information about lesion transmurality, lesion continuity and total energy delivered to the tissue being ablated. In the embodiments presented herein, systems and methods for performing RF ablation while monitoring the procedure using low coherence interferometry (LCI) data are described.

In an embodiment, a catheter includes a distal section, a proximal section, a multiplexer, and a sheath coupled between the distal section and the proximal section. The distal section includes one or more electrodes configured to apply RF energy to a portion of a sample in contact with the one or more electrodes, such that the portion of the sample is ablated. The distal section also includes a plurality of optical elements that transmit one or more beams of exposure radiation away from the distal section of the catheter and receive one or more beams of scattered radiation that have been reflected or scattered from the sample. The proximal section includes an optical source that generates a source beam of radiation and a detector that generates depth-resolved optical data associated with the one or more beams of scattered radiation. The multiplexer generates the one or more beams of exposure radiation from the source beam of radiation.

In another embodiment, a catheter includes a distal section, a proximal section, a processing device, and a sheath coupled between the distal section and the proximal section. The distal section includes one or more electrodes configured to apply RF energy to a portion of a sample in contact with the one or more electrodes such that the portion of the sample is ablated. The distal section also includes a plurality of optical elements configured to transmit one or more beams of exposure radiation away from the distal section of the catheter and receive one or more beams of scattered radiation that have been reflected or scattered from the sample. The proximal section includes an optical source configured to generate a source beam of radiation and a detector configured to generate depth-resolved optical data associated with the one or more beams of scattered radiation. The processing device updates a model of thermal properties of the sample based at least on the depth-resolved optical data.

An example method is described. The method includes transmitting one or more beams of exposure radiation via corresponding openings arranged at a distal end of a catheter. One or more beams of scattered or reflected radiation are received from a sample near the distal end of the catheter. Using a processing device, depth-resolved optical data of the sample is generated based on the received one or more scattered or reflected beams of radiation. The method also determines if the sample is tissue based on the depth-resolved optical data. If the sample is determined to be tissue, then a distance between the distal end of the catheter and the sample is determined based at least on the depth-resolved optical data.

Another example method is presented. The method includes ablating a portion of a sample using RF energy generated from one or more electrodes on a distal end of a catheter, and transmitting one or more beams of exposure radiation via corresponding openings arranged at the distal end of the catheter. One or more beams of scattered or reflected radiation are received from the portion of the sample. Depth-resolved optical data is generated based on the received one or more beams of scattered or reflected radiation. A model of thermal properties of the sample may be provided based at least on the depth-resolved optical data.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIGS. 3A-3B display a distal end of a catheter, according to embodiments.

FIG. 4 displays a distal end of a catheter, according to an embodiment.

Figure 5:
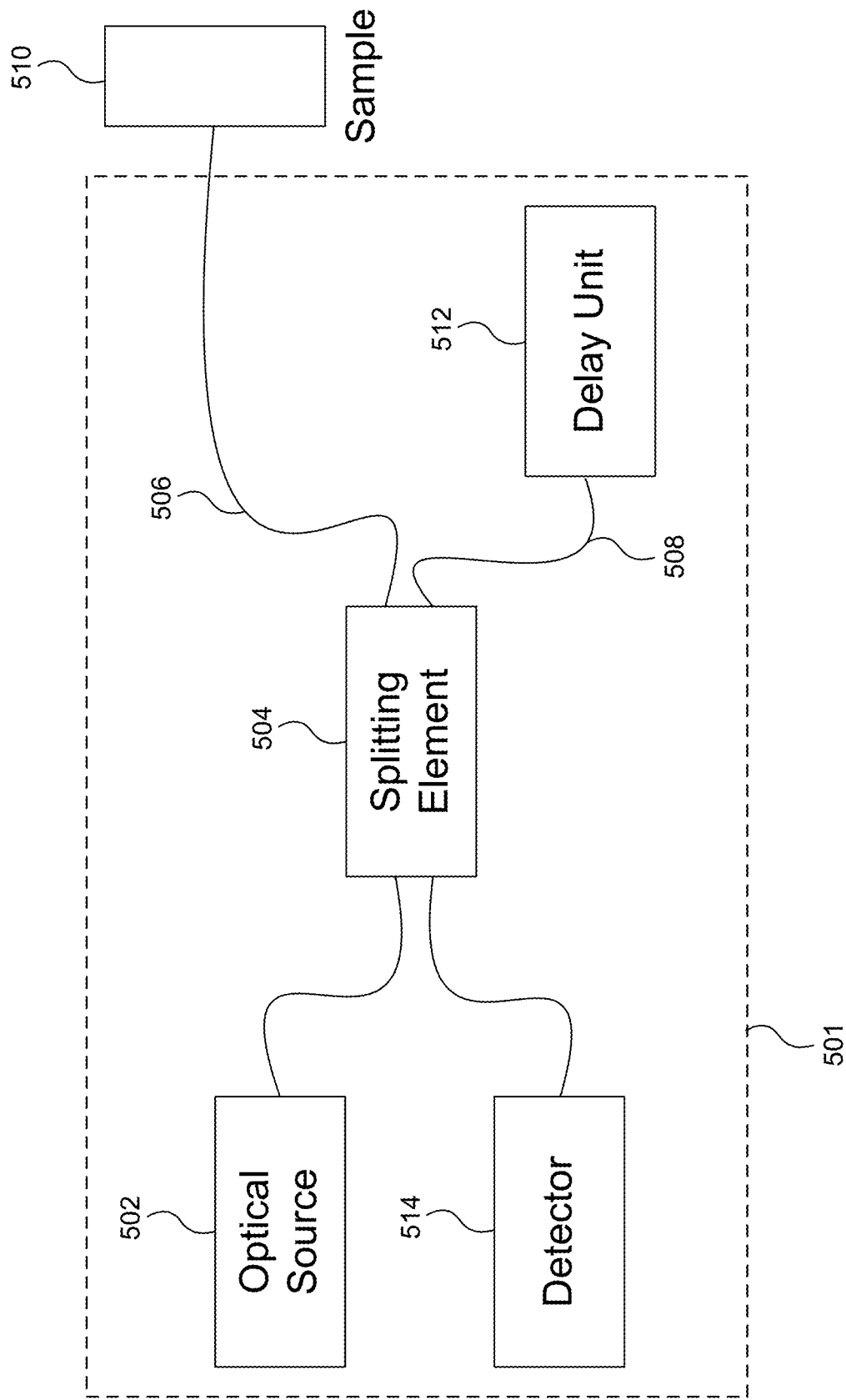

FIG. 5 illustrates a block diagram of a LCI system, according to an embodiment.

Figure 6A:
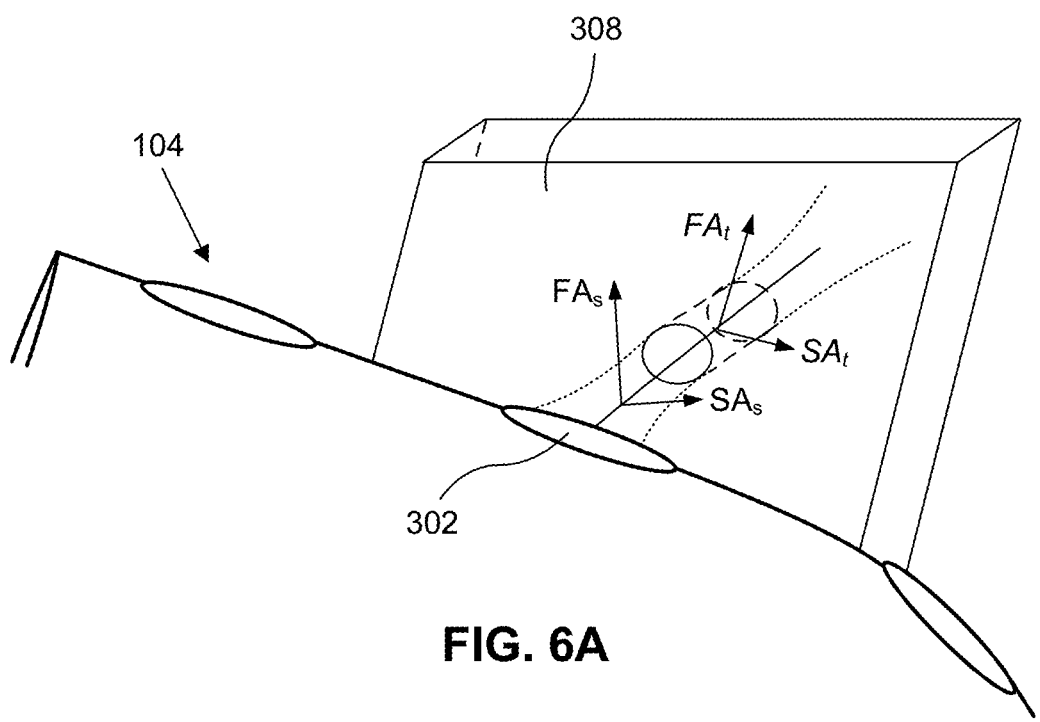
Figure 6B:
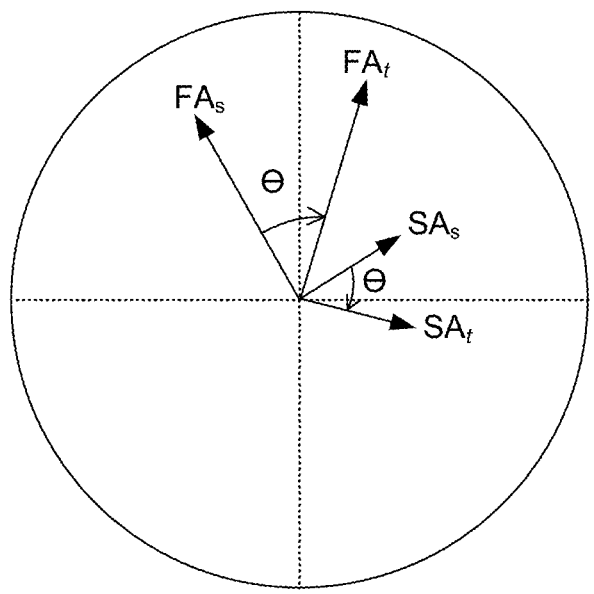

FIGS. 6A-6B illustrate polarization axes of imaging light and a sample

Figure 7:
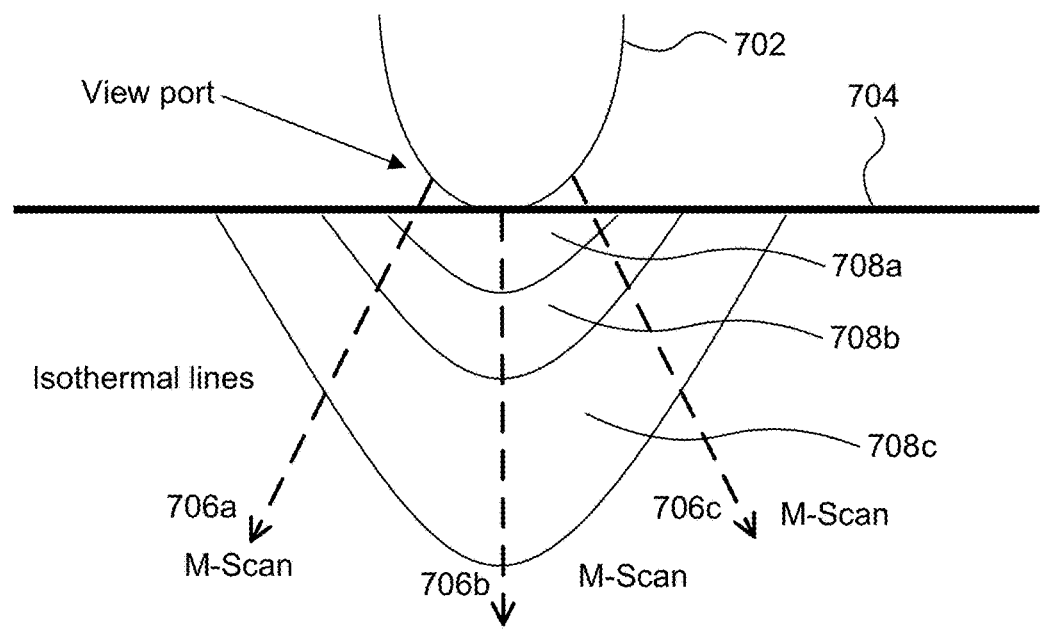

FIG. 7 displays an example temperature distribution in a sample, according to an embodiment.

Figure 8:
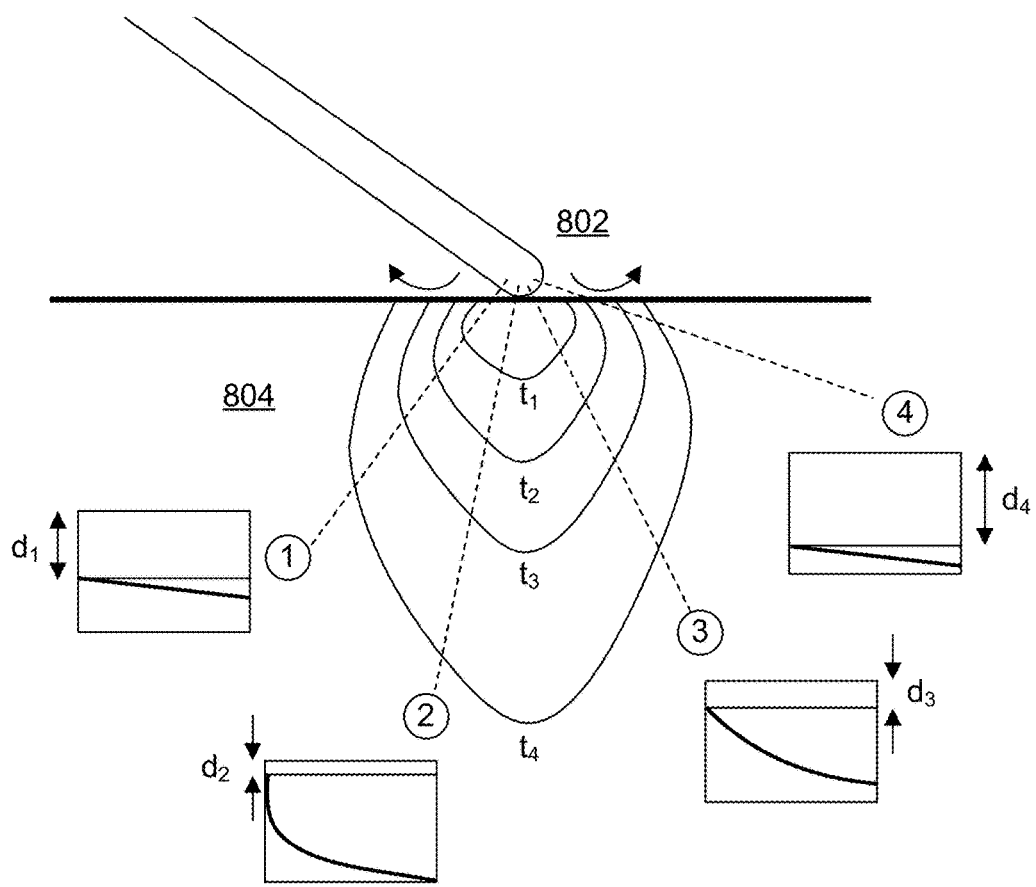

FIG. 8 displays an example temperature distribution in a sample, according to an embodiment.

Figure 9:
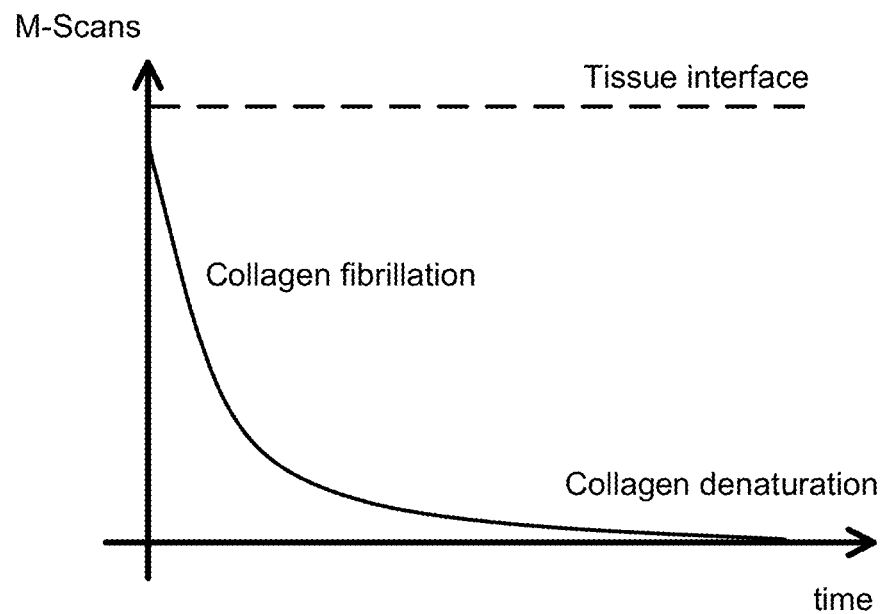

FIG. 9 displays optical results in view of tissue denaturation, according to an embodiment.

Figure 10:
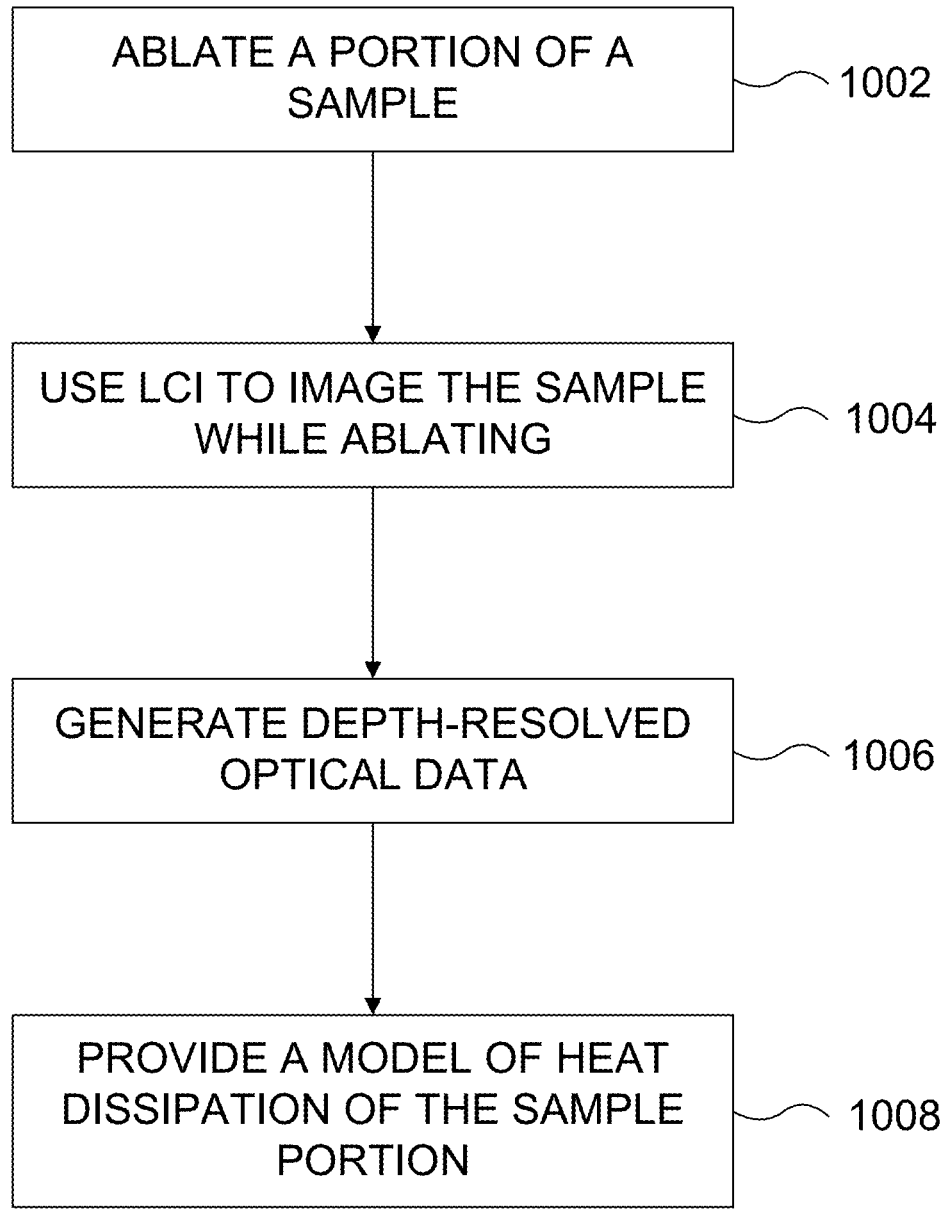

FIG. 10 depicts a method, according to an embodiment.

Figure 11:
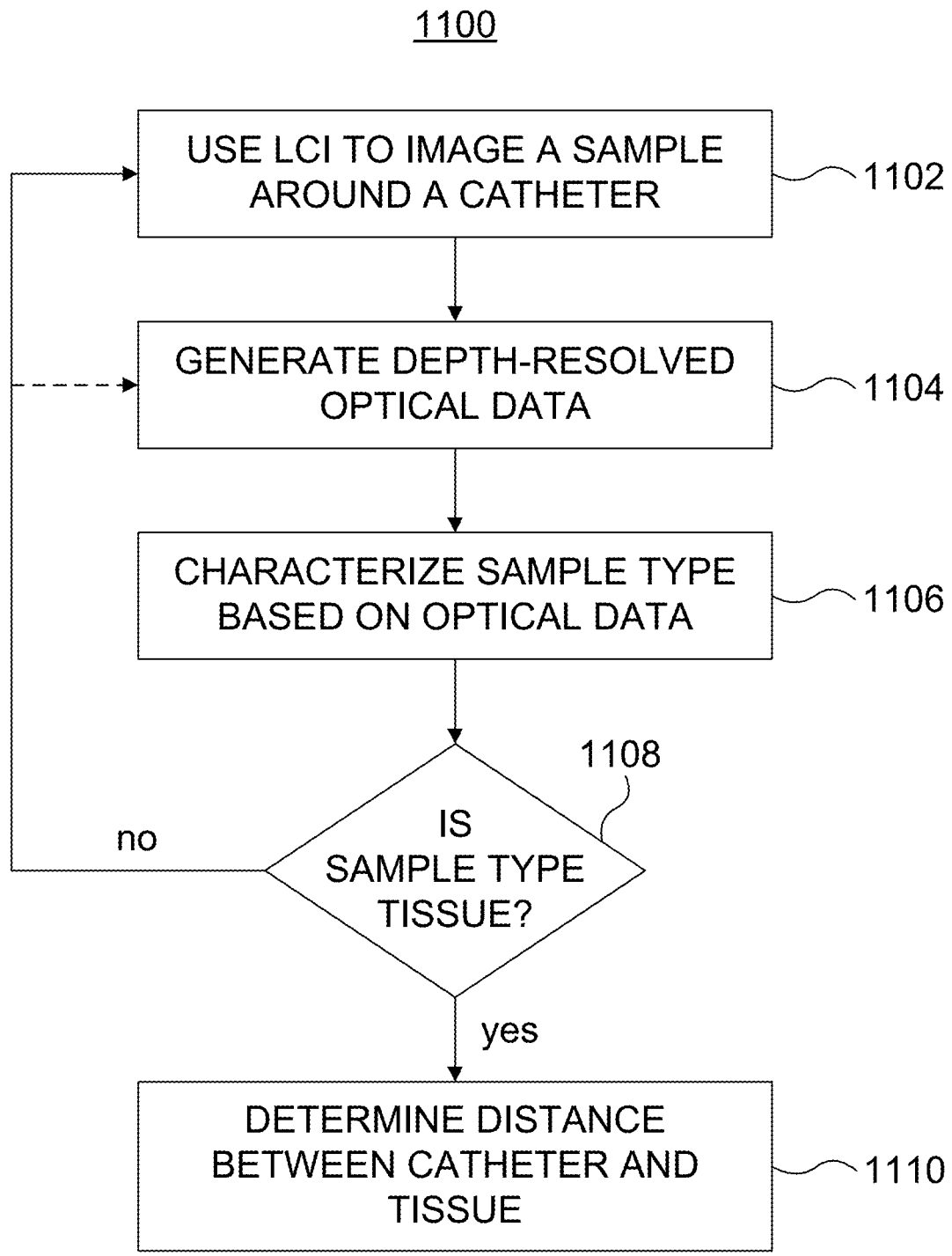

FIG. 11 depicts a method, according to another embodiment.

Figure 12:
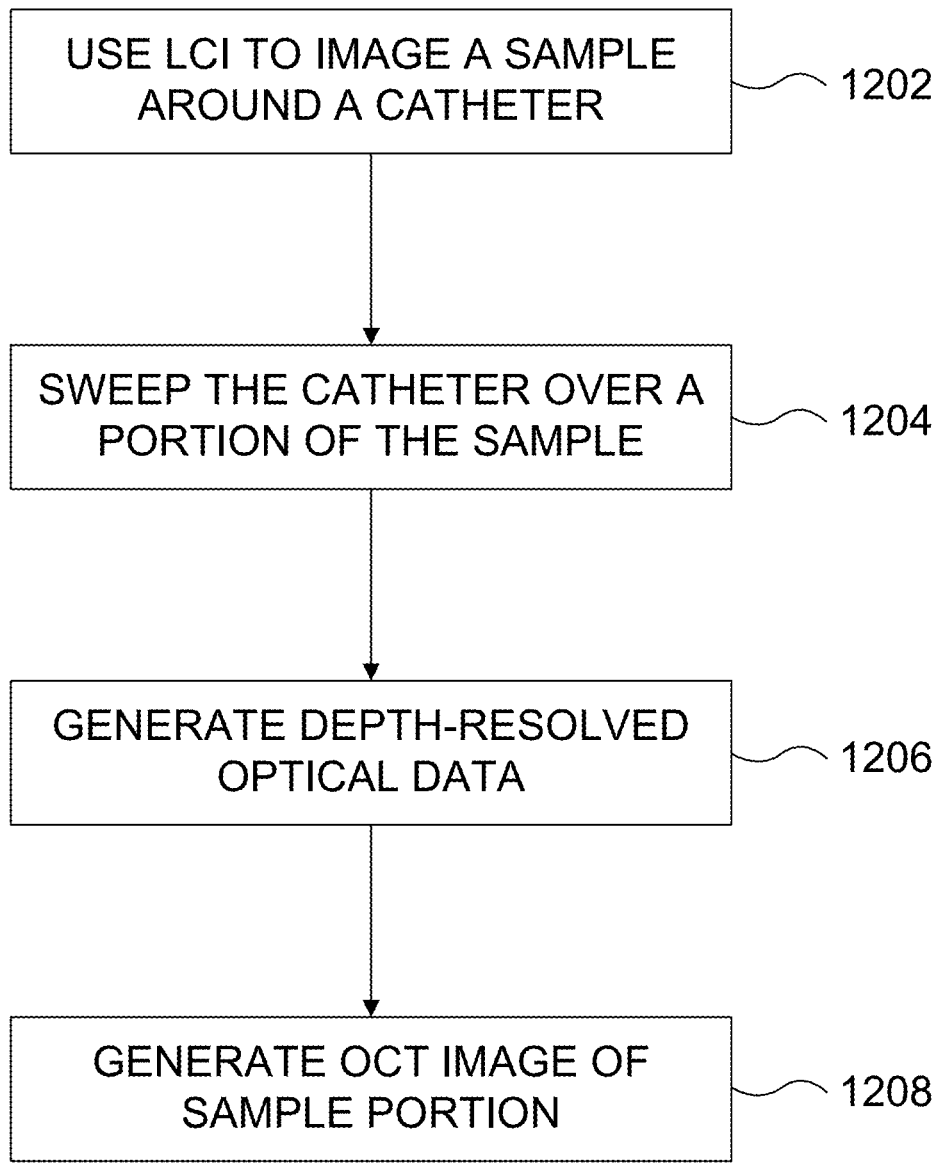

FIG. 12 depicts a method, according to yet another embodiment.

Figure 13:
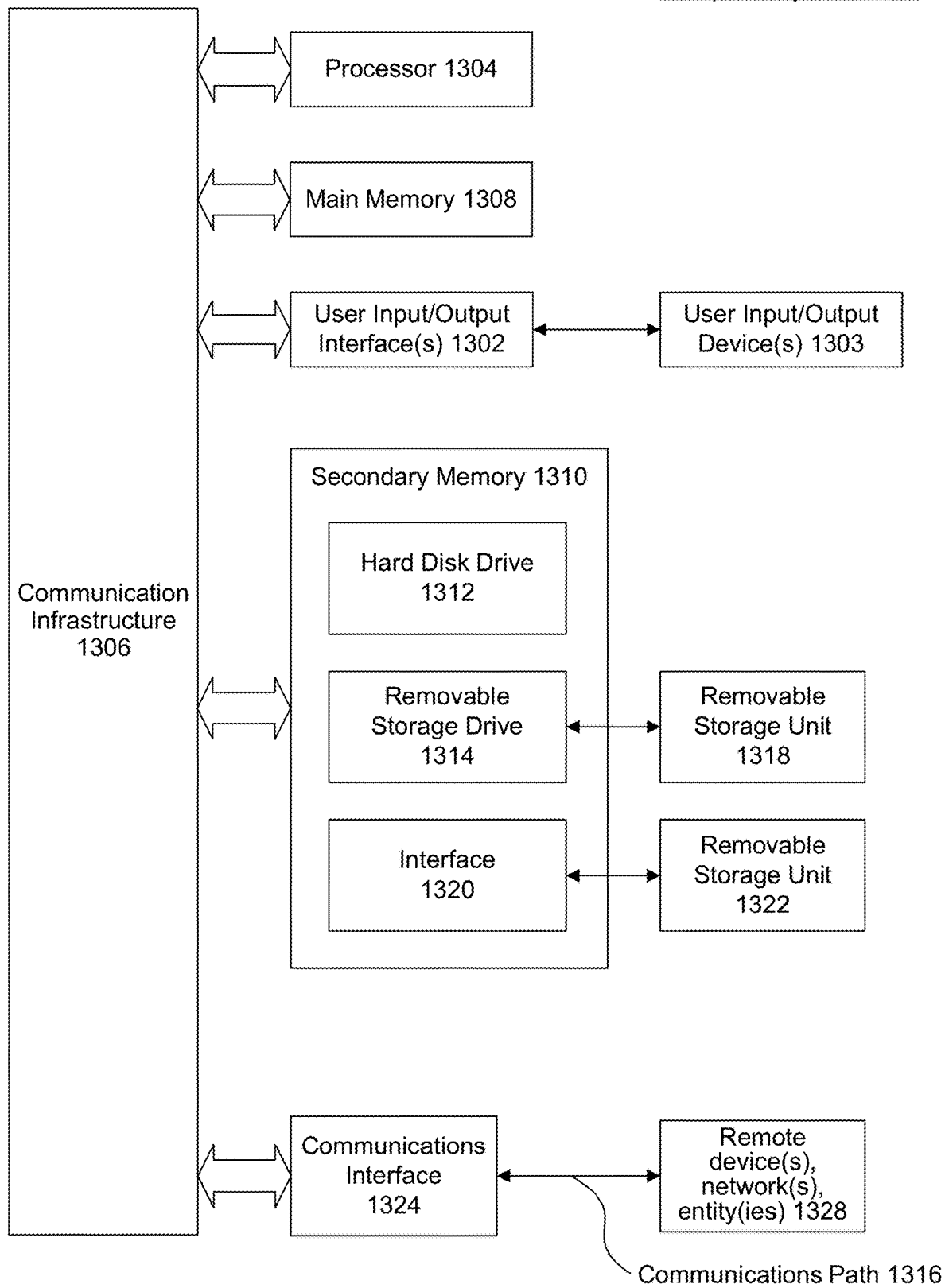

FIG. 13 illustrates an example computer system useful for implementing various embodiments.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

It should be noted that although this application may refer specifically to cardiac ablation, the embodiments described herein may target other pathologies as well. The principles of using RF energy to treat other pathologies are similar, and therefore the techniques used to apply the RF energy are similar.

Described herein are embodiments of a catheter that combines RF ablation with LCI to provide improved control during the ablation procedure. Additionally, methods to combine LCI information with a heat transfer computational model allows estimating energy delivery and temperature distribution in the tissue under ablation. These methods may be implemented by a computing device to provide signal/image processing that feeds information from LCI into a given computational model. The model, or any outputs of the model, may be provided to a user of the catheter, such as a doctor or technician. Alternatively or additionally, any aspects of the model may be used to provide automatic control over the ablation process using, for example, a feedback loop. In some embodiments, the catheter further includes one or a combination of pressure, temperature, position, or shape sensors. Additional subsystems such as, for example, an irrigation system or impedance measurement tools may be included with the catheter. Although embodiments herein describe the use of an RF ablation catheter, other ablation techniques may be utilized as well without deviating from the scope or spirit of the invention, such as, for example, laser ablation.

Herein, the terms "electromagnetic radiation," "light," and "beam of radiation" are all used to describe the same electromagnetic signals propagating through the various described elements and systems.

Catheter Embodiments

Figure 1:
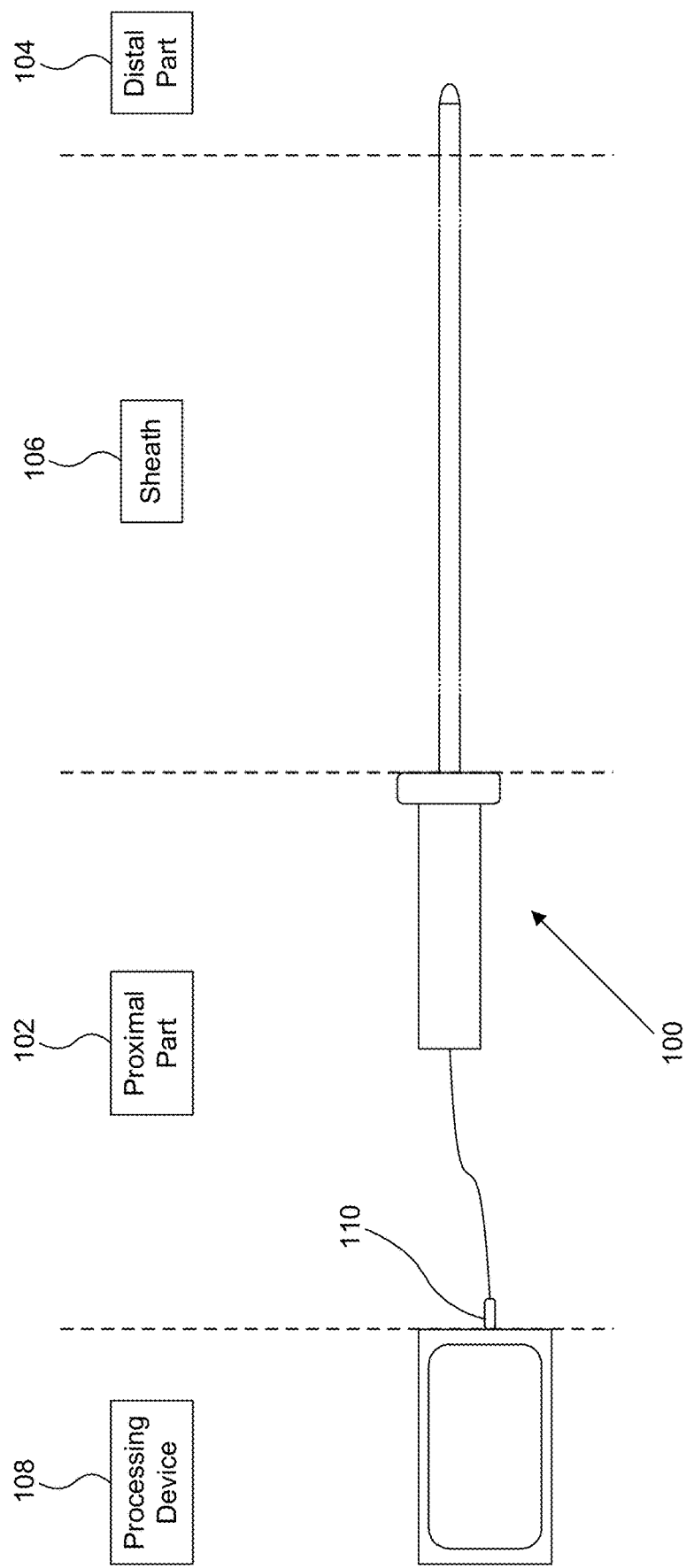
FIG. 1 illustrates a catheter, according to an embodiment.

FIG. 1 illustrates a catheter 100 according to an embodiment. Catheter 100 includes a proximal part 102, a distal part 104, and a sheath 106 coupled between proximal part 102 and distal part 104. In an embodiment, sheath 106 includes one or more radiopaque markers for navigation purposes. In one embodiment, catheter 100 includes a communication interface 110 between catheter 100 and a processing device 108. Communication interface 110 may include one or more wires between processing device 108 and catheter 100. In other examples, communication interface 110 is an interface component that allows wireless communication, such as Bluetooth, WiFi, cellular, etc. Communication interface 110 may communicate with one or more transceiver elements located within either proximal part 102 or distal part 104 of catheter 100.

In an embodiment, sheath 106 and distal part 104 are disposable. As such, proximal part 102 may be reused by attaching a new sheath 106 and proximal part 104 each time a new procedure is to be performed. In another embodiment, proximal part 102 is also disposable.

Proximal part 102 may house various electrical and optical components used in the operation of catheter 100. For example, a power supply may be included within proximal part 102 to apply RF energy to an electrode located at distal part 104 for tissue ablation. The power supply may be designed to generate an alternating current at frequencies at least between 350 and 500 kHz. As such, one or more conductive wires (or any electrical transmission medium) may lead from the power supply to distal part 104 within sheath 106. Furthermore, proximal part 102 may include an optical source for generating a beam of radiation. The optical source may include one or more laser diodes or light emitting diodes (LEDs). The beam of radiation generated by the optical source may have a wavelength within the infrared range. In one example, the beam of radiation has a central wavelength of 1.3 μm. The optical source may be designed to output a beam of radiation at only a single wavelength, or it may be a swept source and be designed to output a range of different wavelengths. The generated beam of radiation may be guided towards distal part 104 via an optical transmission medium connected between proximal part 102 and distal part 104 within sheath 106. Some examples of optical transmission media include single mode and multi-mode optical fibers and integrated optical waveguides. In one embodiment, the electrical transmission medium and the optical transmission medium are provided by the same hybrid medium allowing for both electrical and optical signal propagation.

In an embodiment, proximal part 102 includes one or more components of an interferometer in order to perform LCI using the light generated from the optical source. Further details of the LCI system are discussed with reference to FIG. 5. Due to the nature of interferometric data analysis, in an embodiment the optical transmission medium used for guiding the light to and from distal end 104 does not affect the state and degree of light polarization. In another embodiment, the optical transmission medium affects the polarization in a constant and reversible way.

Proximal part 102 may include further interface elements with which a user of catheter 100 can control the operation of catheter 100. For example, proximal part 102 may include a deflection control mechanism that controls a deflection angle of distal part 104. The deflection control mechanism may require a mechanical movement of an element on proximal part 102, or the deflection control mechanism may use electrical connections to control the movement of distal part 104. Proximal part 102 may include various buttons or switches that allow a user to control when RF energy is applied at distal end 104, or when the beams of radiation are transmitted from distal end 104, allowing for the acquisition of optical data.

Distal part 104 includes one or more external electrodes for ablation, according to an embodiment. For simplicity, in the remainder of the description it is considered that only one ablation electrode is present. Distal part 104 also includes a plurality of optical view ports. In an embodiment, one or more of the optical view ports are machined in each of the one or more electrodes.

The electrode used for ablation is in electrical connection with at least one cable running along the length of sheath 106. The optical view ports are distributed over the outside of distal part 104, resulting in a plurality of distinct viewing directions, according to an embodiment. In an embodiment, each of the plurality of viewing directions are substantially non-coplanar. The optical view ports may also be designed with irrigation functionality to cool distal part 104 and surrounding tissue from overheating during ablation. Further details on the design of distal part 104 are discussed with reference to FIGS. 3A, 3B, and 4.

Figure 2A:
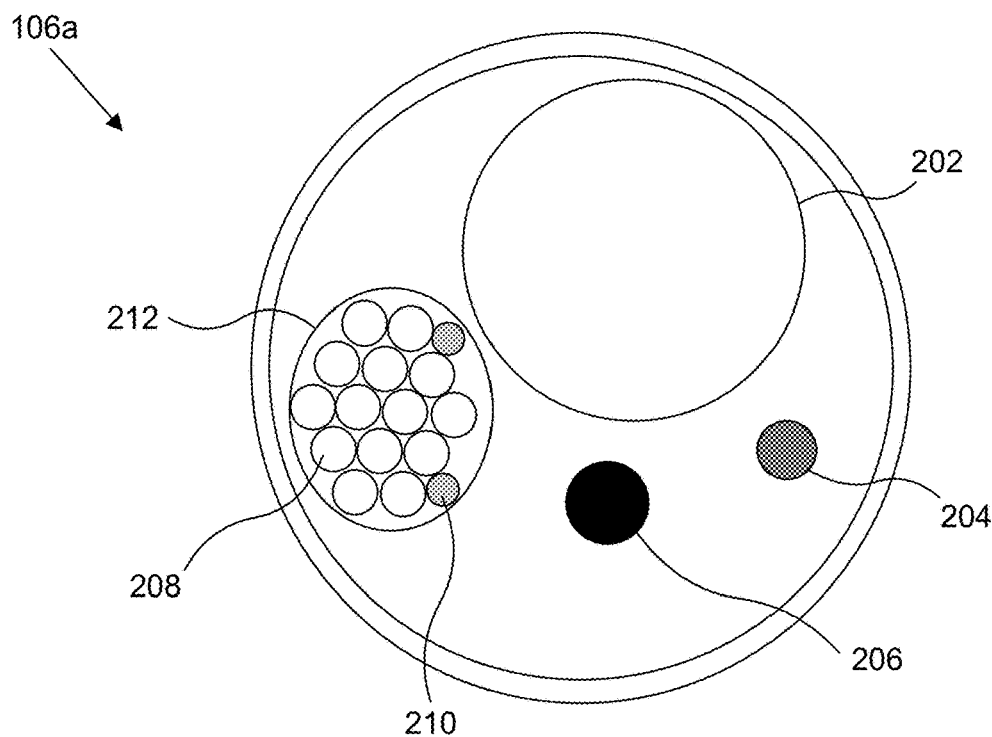
FIGS. 2A-2B illustrate cross sections of a catheter, according to embodiments.
Figure 2B:
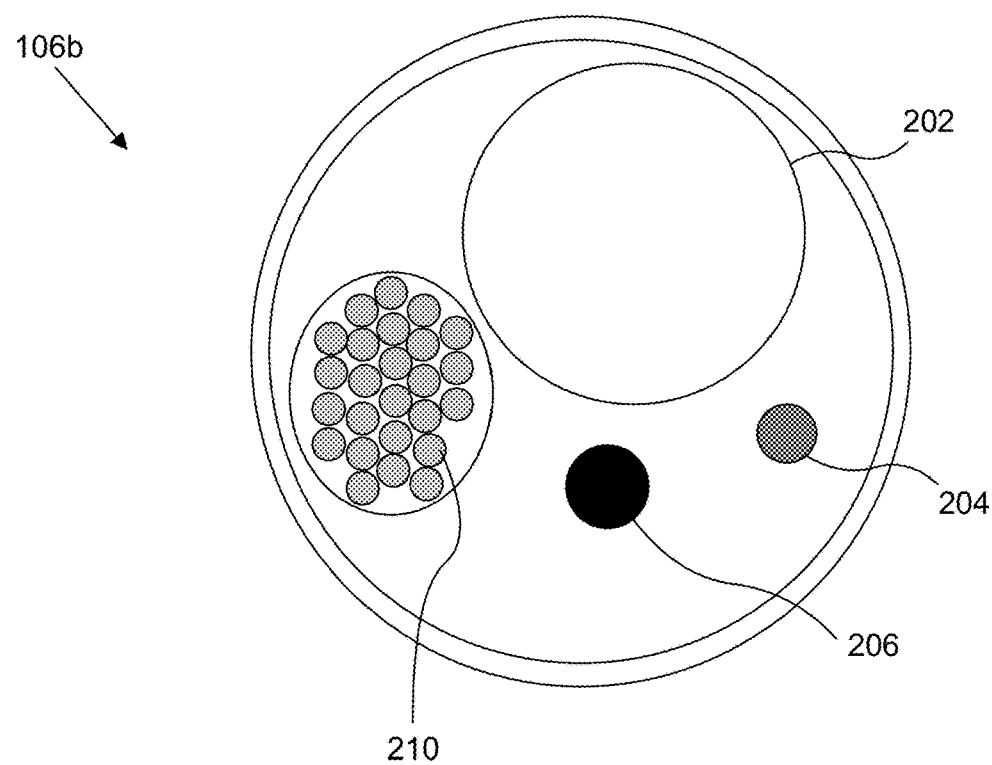

FIGS. 2A and 2B illustrate cross-section views of sheath 106, according to embodiments. Sheath 106 may include all of the elements interconnecting proximal part 102 with distal part 104. Sheath 106a illustrates an embodiment that houses an irrigation channel 202, RF conductive medium 204, deflection mechanism 206, electrical connections 208, and optical transmission medium 210. FIG. 2A illustrates a protective cover 212 wrapped around both electrical connections 208 and optical transmission media 210. Electrical connections 208 may be used to provide signals to optical modulating components located in distal part 104. One or more optical transmission media 210 guide light generated from the optical source (exposure light) towards distal part 104, while another subset of optical transmission media 210 guides light returning from distal part 104 (scattered or reflected light) back to proximal part 102. In another example, the same one or more optical transmission media 210 guides light in both directions.

Irrigation channel 202 may be a hollow tube used to guide cooling fluid towards distal part 104. Irrigation channel 202 may include heating and/or cooling elements disposed along the channel to affect the temperature of the fluid. In another embodiment, irrigation channel 202 may also be used as an avenue for drawing fluid surrounding distal part 104 back towards proximal part 102.

RF conductive medium 204 may be a wire or cable used to provide RF energy to the ablation electrode located at distal part 104. Deflection mechanism 206 may include electrical or mechanical elements designed to provide a signal to distal part 104 in order to change a deflection angle of distal part 104. The deflection system enables guidance of distal part 104 by actuating a mechanical control placed in proximal part 102, according to an embodiment. This system may be based on a series of aligned and uniformly spaced cutouts in sheath 106 aimed at providing unidirectional deflection of distal part 104, in combination with a wire which connects the deflection mechanism control in proximal part 102 with the catheter tip at distal part 104. In this way, a certain movement of the proximal part may be projected to the distal part. Other embodiments involving the combination of several control wires attached to the catheter tip may enable the deflection of the catheter tip along different directions.

FIG. 2B illustrates a cross-section of sheath 106b. Sheath 106b depicts an embodiment having most of the same elements as sheath 106a from FIG. 2A, except that there are no electrical connections 208. Sheath 106b may be used in situations where modulation (e.g., multiplexing) of the generated beam of radiation is performed in proximal part 102.

FIGS. 3A and 3B illustrate views within distal part 104, according to embodiments. FIG. 3A illustrates distal part 104a. Distal part 104a depicts an embodiment having a plurality of view ports 302, a plurality of optical fibers 304, an electrode 306 which also acts as an outer body of distal part 104, and one or more irrigation channels 310 located substantially at a tip of distal part 104a. Plurality of view ports 302 may be arranged around the outside of distal part 104a in any pattern to achieve various views of a sample 308. RF energy may be applied to electrode 306 to ablate a portion of sample 308. Electrode 306 may represent one or more electrodes on distal part 104a. In an embodiment, optical fibers 304 may be any other type of waveguiding structures, such as waveguides defined within an optical integrated circuit. In another embodiment, optical fibers 304 may be waveguiding structures defined upon a flexible substrate. A multiplexing unit 312 may also be defined upon the same flexible substrate that includes the waveguiding structures.

Optical fibers 304 are used at each of plurality of view ports 302 to both transmit and receive light through each of plurality of view ports 302. Exposure light is transmitted through view ports 302 away from distal part 104a and onto sample 308, while light that is scattered or reflected by sample 308 is received through view ports 302. Each view port of plurality of view ports 302 may include more than one optical fiber, for example, a fiber bundle. Light generated from the optical source within proximal part 102 may be split amongst each of the view ports 302 using the multiplexing unit 312. Alternatively, multiplexing unit 312 may select one of the plurality of view ports 302 for light to travel either to or from. Multiplexing unit 312 receives an input beam of radiation via optical transmission line 316. Optical transmission line 316 may include any number of optical transmission elements (e.g., optical fibers), and may be similar to optical transmission media 210 of FIGS. 2A and 2B. Electrical wires 318 may be included to carry control signals to multiplexing unit 312 from proximal part 102 of catheter 100.

Multiplexing unit 312 may include associated electronics 314 that provide control signals to various modulating elements of multiplexing unit 312. Multiplexing unit 312 may use any multiplexing method that allows for the separation of contributions from the light collected by the various view ports 302. One such multiplexing method is time-domain multiplexing, in which multiplexing unit 312 switches between different output waveguides in a controlled manner, so that at a given time only one of the associated view ports 302 is active. Another suitable multiplexing method is frequency-domain multiplexing, in which light traversing each of view ports 302 is modulated in such a way that the time-frequency behavior of signals corresponding to different view ports 302 can be differentiated by a processing device. Coherence-domain multiplexing may also be used in multiplexing unit 312, by introducing a different group delay to the light traversing each view port 302, so that the signals corresponding to different view ports 302 appear at different coherence positions and can be therefore differentiated by a processing device. In an embodiment, these methods are non-exclusive and can be combined in order to find the best design compromise. Some of the multiplexing methods, like coherence-domain multiplexing, do not require any electrical actuation of multiplexing unit 312. Thus, in an embodiment, implementations based on coherence-domain multiplexing do not require electrical transmission media for control signals.

In one embodiment, multiplexing unit 312 is produced on a silicon photonics optical chip using a network of thermoelectric optical switches. Other suitable materials for use in multiplexing unit 312 include silicon nitride, silicon dioxide, oxinitride, lithium niobate, III-V semiconductor materials, silicon carbide and optical grade polymers. Other modulation effects to support the optical switching operation include the electro-optic effect, charge carrier density effects, photo-mechanical effects, liquid crystal based refractive index modulation, etc. The multiplexing function may also be obtained through microelectromechanical (MEMS) devices in as far as miniaturization and packaging constraints can be met. The connections between electrical wires 318 and multiplexing unit 312 may be achieved via individual wire-bonding or soldering, or through an intermediate substrate that allows for flip-chip assembly in an individual or batch process. In an embodiment, this intermediate substrate is flexible.

In an embodiment, multiplexing unit 312 is fabricated upon a flexible substrate. A process for forming the optical elements upon a flexible substrate includes a substrate transfer post-processing step applied to Silicon on Insulator (SOI) chips or wafers, as described in more detail in co-pending U.S. application Ser. No. 13/761,054, the disclosure of which is incorporated by reference herein in its entirety. In an embodiment, the resulting flexible device is thinner (<100 µm) than the starting thickness (500-700 µm). Multiplexing unit 312 may be implemented by an optical integrated chip that is partly flexible. Plurality of optical fibers 304 are suitably flexible in order to reach the various view ports 302 arranged round distal part 104*a*, according to an embodiment. Associated electronics 314 may be attached to either the bottom side or top side of an integrated chip that includes multiplexing unit 312. In another embodiment, both multiplexing unit 312 and associated electronics 314 are disposed upon a flexible substrate. In one example, the flexible substrate having both multiplexing unit 312 and associated electronics 314 is rolled in a cylindrical shape to fit within distal part 104*a* of catheter 100.

Distal part 104*a* may include one or more irrigation channels 310 to deliver fluid to a plurality of holes (not shown) on the outside of distal part 104*a*. The fluid delivered via irrigation channels 310 may be used for cooling during the ablation procedure. In other embodiments, irrigation channels 310 may be designed to deliver therapeutic fluids to sample 308.

Distal part 104*a* may also include a force sensor 317. In an embodiment, force sensor 317 is designed to measure a force applied to distal part 104*a* during operation along one or more reference axes. Force sensor 317 may include a rigid element coming from the sheath (e.g. a rigid wire) mechanically connected to a part of the sensor, while an external electrode is connected to a different part of the sensor. The general assembly of the catheter and any mechanical fixation element acting between electrode 306 and the sheath must ensure sufficient stress transfer to force sensor 317. In another embodiment, force sensor 317 may be a pressure sensor based on, for example, a strain gauge.

Force sensor 317 may have its readout element defined in the same substrate as multiplexing unit 312, according to an embodiment. The read-out principle may be based on an interferometric analysis of distance change associated to strain, on a piezo-electric device, on a capacitance measurement, or based on an electromagnetic measurement. According to an embodiment, the signals generated from force sensor 317 propagate through additional cables and/or optical transmission media running through sheath 106. Alternatively, the signals may propagate through the same electrical and optical paths used for multiplexing unit 312 and its associated electronics 314. In the latter case, the multiplexed optical path and force sensor 317 data path may be separated through a suitable signal multiplexing technique. Additionally, if irrigation channels 310 are perfused at a low and constant flow, the pressure may be measured indirectly by adding a pressure transducer in proximal part 102 of catheter 100.

In an embodiment, a temperature sensor 319 may be included in distal part 104*a*, measuring the temperature substantially at the tip of the catheter during operation. Temperature sensor 319 may be a thermo-couple, an element with a known resistive dependence on temperature, an element where an optical parameter changes with temperature, or any other type of temperature sensor. Temperature sensor 319 may be included as an element defined in the same substrate as multiplexing unit 312. According to an embodiment, the signals generated from temperature sensor 319 propagate through additional cables and/or optical transmission media running through sheath 106, or through the same electrical and optical paths used for multiplexing unit 312 and its associated electronics 314. In the latter case, the multiplexed optical path and temperature sensor 319 data paths may be separated through a suitable signal multiplexing technique.

FIG. 3*b* illustrates another embodiment of the distal part, depicted as distal part 104*b*. Distal part 104*b* includes many of the same elements as those described in distal part 104*a*. However, distal part 104*b* does not include multiplexing unit 312 and associated electronics 314. A bundle of fibers 320 is used to provide light to the plurality of optical fibers 304 within distal part 104*b*. In a catheter embodiment using distal part 104*b*, a multiplexing unit may be located within proximal part 102 or external to catheter 100 (such as, for example, with processing device 108).

In either embodiment of distal part 104 illustrated in FIGS. 3A and 3B, the plurality of view ports 302 may include one or more lenses and/or mirrors designed to focus the light traversing any of view ports 302. The material used within each view port 302 is substantially transparent to the wavelength of light used for optical interrogation, according to an embodiment. The lenses may be coated with an antireflective layer to minimize optical losses. The mirrors may be locally produced through the selective evaporation of a metal layer through a mask on the surfaces to be made reflective, and may be flat or provide a focusing function. The body of distal part 104 may be formed using injection molded plastic, and designed to support the packaging of multiplexing unit 312. In an embodiment, the lenses used at the plurality of view ports 302 include gradient index lenses and/or lenses with tapered tips.

In an embodiment, one or more of the plurality of view ports 302 includes a scanning element (not shown) that allows for the beam of radiation exiting through view port 302 (the exposure radiation) to be scanned in a given direction. The scanning element may include a microelectromechanical system (MEMS) component, or use electro-optical modulators to steer the exit angle of the beam of radiation from an associated view port. Further details and examples regarding the scanning of the beams of radiation may be found in co-pending U.S. application Ser. No. 14/118,629, the disclosure of which is incorporated by reference herein in its entirety.

FIG. 4 illustrates a view of the outside of distal part 104, according to an embodiment. Plurality of view ports 302 may be located anywhere around the entire outer surface of distal part 104 to provide any number of angles for viewing a tissue sample (e.g., an atrial wall) around distal part 104. Additionally, distal part 104 may include a plurality of openings 402 that are associated with irrigation channels 310 shown in FIGS. 3A and 3B. Openings 402 may also be placed anywhere around the outer surface of distal part 104 and used to either expel liquid to the area surrounding distal part 104, or to draw liquid from the area surrounding distal part 104.

LCI System Embodiment

Various embodiments of the present application include a LCI system integrated within catheter 100 for optical interrogation of the tissue surrounding distal part 104. FIG. 5 illustrates an example LCI system 501 for imaging a sample 510, according to an embodiment. For example, sample 510 may be a portion of an atrial wall to be ablated. A delay unit 512 may include various light modulating elements. These modulating elements may perform phase and/or frequency modulation to counteract undesired optical effects in the light, and to select one or more depths of sample 510 to be imaged. The use of the term "light" may refer to any range of the electromagnetic spectrum. In an embodiment, the term "light" refers to infrared radiation at a wavelength of about 1.3 µm.

LCI system 501 further includes an optical source 502, a splitting element 504, a sample arm 506, a reference arm 508, and a detector 514. In the embodiment shown, delay unit 512 is located within reference arm 508. However, it should be understood that delay unit 512 may instead be located in sample arm 506. Alternatively, various elements of delay unit 512 may be present in both sample arm 506 and reference arm 508. For example, elements of delay unit 512 that introduce a variable delay to the light may be located in sample arm 506, while elements that modulate different polarization modes of the light may be located in reference arm 508. In one example, sample arm 506 and reference arm 508 are optical waveguides, such as patterned waveguides or optical fibers. In an embodiment, all of the components of LCI system 501 are integrated onto a planar lightwave circuit (PLC). In another embodiment, at least the components within delay unit 512 are integrated on the same substrate of a PLC. Other implementations may be considered as well, such as, for example, fiber optic systems, free-space optical systems, photonic crystal systems, etc.

It should be understood that LCI system 501 may include any number of other optical elements not shown for the sake of clarity. For example, LCI system 501 may include mirrors, lenses, gratings, splitters, micromechanical elements, etc., along the paths of sample arm 506 or reference arm 508.

Splitting element 504 is used to direct light received from optical source 502 to both sample arm 506 and reference arm 508. Splitting element 504 may be, for example, a bi-directional coupler, an optical splitter, or any other modulating optical device that converts a single beam of light into two or more beams of light.

Light that travels down sample arm 506 ultimately impinges upon sample 510. Sample 510 may be any suitable sample to be imaged, such as tissue. The light scatters and reflects back from various depths within sample 510 and the scattered/reflected radiation is collected back into sample arm 506. In another embodiment, the scattered/reflected radiation is collected back into a different waveguide than the transmitting waveguide. The scan depth may be chosen via the delay imposed on the light within delay unit 512.

Light within sample arm 506 and reference arm 508 is recombined before being received at detector 514. In the embodiment shown, the light is recombined by splitting element 504. In another embodiment, the light is recombined at a different optical coupling element than splitting element 504. Detector 514 may include any number of photodiodes, charge-coupling devices, and/or CMOS structures to transduce the received light into an electrical signal. The electrical signal contains depth-resolved optical data related to sample 510 and may be received by a processing device for further analysis and signal processing procedures. As used herein, the term "depth-resolved" defines data in which one or more portions of the data related to specific depths of an imaged sample can be identified.

In an embodiment, optical source 502, detector 514 and delay unit 512 are located within proximal part 102 of catheter 100. Splitting element 504 and at least part of one or both of sample arm 506 and reference arm 508 may be located in either proximal part 102 or distal part 104 of catheter 100. In another embodiment, all of the elements of LCI system 501 are located in distal part 104 of catheter 100. Optical source 502 may include one or more light emitting diodes (LEDs) or laser diodes. For example, LEDs may be used when performing time domain and/or spectral domain analysis, while tunable lasers may be used to sweep the wavelength of the light across a range of wavelengths. In another embodiment, optical source 502 and detector 514 are located external to catheter 100, for example, with processing device 108.

LCI system 501 is illustrated as an interferometer design similar to a Michelson interferometer, according to an embodiment. However, other interferometer designs are possible as well, including Mach-Zehnder or Mireau interferometer designs.

Example Methods and Modes of Operation

Catheter 100 may be used to perform ablation by applying high-frequency alternating current to tissue in contact with distal part 104 of catheter 100. Oscillating frequencies ranging from 350 to 500 kHz may be used. It should be understood that other frequencies may be used as well and that any frequencies above about 1 kHz rarely produce electrical stimulation of excitable cells. An adjustable-power high-frequency power source providing the RF energy to electrode 306 at distal part 104 may be used. The physics underlying the heat transfer to tissue is based on a high electrical impedance of the tip-tissue interface. The impedance of this tissue-electrode interface, at the ablation frequency, may be substantially greater than that of the returning electrode. For a given current delivered though the body, a greater voltage drop may be generated at this interface producing heat at the desired location. In this way, a small tissue volume surrounding the catheter tip is ablated, instead of all the tissue volume from the catheter tip to the ground contact, which is typically placed on the patient's back during cardiac ablation treatment. By adjusting the RF power and ablation time, the total energy delivered to tissue may be accurately controlled. Other ablation techniques based on cryogenic or optical means (e.g., laser ablation) may also be used for the treatment of different pathologies.

In embodiments where optical multiplexing unit 312 within catheter 100 uses time-domain multiplexing, only a subset of view ports 302 in contact with tissue will be considered while ablation is occurring, according to one embodiment. In this way, the line acquisition rate may be maximized for the active view ports during the ablation process. The sequence of LCI lines of the region subject to ablation may be collected over a period of time. Signal processing algorithms may be used to monitor lesion progress by looking at changes in the signal over time. Such algorithms may be executed by processing device 108. For example, an M-scan involves a repeated axial scanning at the same physical location as a function of time. In particular, an M-scan representation may be constructed with acquisition starting immediately before RF energy delivery. According to an embodiment, the signal and image processing software, executed by processing device 108, receives timing information associated with the application of RF energy by catheter 100. In this way, data may be collected only during the times that tissue ablation is occurring.

In an embodiment, the signal and image processing software accounts for the birefringence of the tissue. The birefringence of the tissue fibers may be altered due to a number of potential factors outside of the ablation procedure. It is known that connective biological fibers such as collagen exhibit birefringent properties. When full tissue necrosis is attained by heat transfer, collagen fibers denature. This denaturation produces a loss of the birefringent behavior of these fibers. Irreversible denaturation of collagen fibers occurs at about 60° C. Cell death is caused by a combination of an applied supra-physiological temperature and its duration. However, a partial loss of birefringence may be indicative of partial tissue damage (edema), which may ultimately compromise the efficacy of the procedure. In one example, at temperatures lower than 60° C., collagen denaturation caused by triple helix hydrogen bonds break down and may reduce birefringence in a reversible way. In other examples, the combination of both the exposure time and the elevated temperature produces denaturation and cell death.

The use of polarization sensitive LCI (PS-LCI) techniques allows for the monitoring of birefringent changes in the tissue, and therefore may lead to an estimation of the degree of denaturation induced in the tissue. In an embodiment, the signal and image processing software is capable of combining data regarding polarization-related tissue properties with structural data associated with a total amplitude of the depth-resolved optical data collected by the LCI system. The data regarding polarization of the tissue fibers may also be extracted from the depth-resolved optical data. An image of the sample may be generated by a processing device based on a difference in the birefringent properties of various portions of the sample. For example, the birefringence exhibited by the ablated sample portion is different from the birefringence exhibited by non-ablated portions of the sample.

Birefringent materials may be characterized by two orthogonal linear polarizations having a certain orientation. Each polarization features a different refractive index, known as slow and fast axes. FIGS. 6A and 6B illustrate this concept, according to an embodiment. In FIG. 6A, distal part 104 of a catheter is shown with light exiting from one of the plurality of view ports 302 onto sample 308. In both FIGS. 6A and 6B, $FA_s$ and $SA_s$ represent the fast axis and slow axis, respectively, of the LCI System. $FA_t$ and $SA_t$ represent the fast axis and slow axis, respectively, associated with sample 308. Sample 308 may be, for example, a tissue sample.

Tissue-specific contrast may be dependent on the magnitude of the tissue birefringence, as well as on the orientation of the birefringence axes of the tissue ($FA_t$ and $SA_t$) in relation to the polarization state of the incident light. However, the birefringence axes of the tissue might change with time due to the stress generated by the catheter and the temperature. Additionally, the polarization state of the incident light may change with time due to the temperature and the stress generated in optical transmission media during the imaging procedure. This forms an angle mismatch (A in FIG. 6B) between the axes of the incident light and the related axes associated with sample 308.

In an embodiment, a correcting module configured to correct the angle mismatch θ is implemented within the LCI system. The correcting module may be implemented in hardware, for example, with on-chip polarization components. The on-chip components may be part of the delay unit 512 in LCI system 501. In another example, the correcting module may be implemented with fiber-based polarization controllers. In another example, the correcting module may be implemented in software and executed by a computing device, such as processing device 108 in FIG. 1.

According to an embodiment, the correcting module is designed to rotate the polarization state of the incident light in the range of π/2 radians while monitoring the birefringence of the backscattered signal from the sample. As a result of this polarization orientation sweep, the polarization state exhibiting an optimum value (e.g., a maximum signal contrast) may be obtained and fixed. Alternatively, a continuous sweep of the polarization state of the incident light may also be used in synchronization with optical data acquisition.

Thermal Modeling

The collected depth-resolved optical data may also be used at a processing device to generate and/or enhance a thermal model of heat dissipation within the ablated sample, according to an embodiment. The speed and extent of changes detected in the LCI signals are excellent indicators of thermal power delivery to tissue, and can be quantified based on, for example, the bio-heat model, as in equation 1 below.

$$\rho \cdot c \frac{\partial T}{\partial t} = \nabla \cdot k \nabla T + q - Q_p + Q_w \quad (1)$$

This equation represents the heat transfer in a biological sample using an external source. In this equation, ρ is the mass density, c is the specific heat, T is the temperature, k represents the thermal conductivity, q is the heat source (Joule's effect), $Q_p$ is the convection heat loss, and $Q_w$ is the metabolic heat.

According to an embodiment, changes in the polarization of the received light from the sample may be linked to a specific temperature threshold in the tissue being ablated, which in turn may be linked to a defined denaturation process of the biomolecules. Based on the time to induce this process at a given distance from the ablation electrode and the general progression of the lesion over time and depth, a good assessment of power transfer may be made.

FIG. 7 illustrates how heat is delivered to the tissue from an ablation catheter tip 702, according to an embodiment. Catheter tip 702 is brought into contact with a sample surface 704, for example, a tissue interface, and RF energy is delivered to the sample to ablate a portion of the sample. A heat gradient generated by the delivery of the RF energy is formed in the sample as depicted by the isothermal boundary areas 708a-c. For example, boundary area 708a may be associated with the hottest temperatures generated by the application of the RF energy while boundary areas 708b and 708c represent progressively cooler temperatures. Catheter tip 702 also includes a plurality of view ports, such as those described earlier with reference to FIGS. 3A and 3B, that allow for M-scans 706a-c to be taken at different angles and/or locations within the sample, according to an embodiment. Each M-scan may be considered to be equivalent to the received scattered/reflected light returning from multiple depths within the sample.

In an embodiment, the data received from M-scans 706a-c provide information of the denaturation process occurring along each scanned line. For example, the data received from each M-scan 706a-c may be used to generate and/or enhance a thermal model of the heat distribution present in the sample.

FIG. 8 illustrates another example of how heat is delivered to tissue 804 from an ablation catheter tip 802 and monitored using four view ports (1-4). In an embodiment, the relative position of catheter tip 802 is inferred by computing the first light reflection at each view port (1-4) that defines a distance from the view port to tissue 804. This may provide an estimation of tissue contact and therefore an approximation of the impedance of the tissue-electrode interface. In an embodiment, distances d1, d2, d3 and d4 represent the first reflection and therefore the distance from each associated viewport to tissue 804. Curves labeled t1 to t4 represent the profile of the denaturation temperature at times t1 to t4. In an embodiment, the illustrated curves obtained at each viewport (1-4) represent of the variation of the phase/delay difference measured in PS-LCI against time. Different decay rates are observed depending on the direction of the M-scan coming from each of viewports (1-4). These decay rates may also depend on irrigation, which cools down the surface and leads to a more conical-like heat diffusion pattern. In an embodiment, the correlation of the information obtained by the PS-LCI signal from each view port (1-4) provides spatial sampling of the isothermal line at which collagen denatures. By using the PS-LCI data, the dynamics of collagen denaturation, energy delivery, and/or tissue ablation may be estimated.

FIG. 9 illustrates an example curve representing the average phase/group delay obtained from the M-scans against ablation time. Data regarding the change in certain parameters over time, such as that illustrated in FIG. 9, may be used to generate and/or enhance the thermal model of the sample during ablation.

The thermal model may be presented to a user of the catheter to provide further information regarding the ablation procedure. In another embodiment, data from this thermal model may be used to automatically control the ablation process. For example, the thermal model may be used to control a duty cycle of the applied RF energy, or to shut off the application of the RF energy if the temperature increases above a threshold.

General thermal properties of the tissue sample, including heat capacity and heat diffusivity, together with other heat transfer effects derived from the thermal model, such as convection close to the surface, may be used to further compute relevant clinical parameters, such as depth and width of the created lesion. The known thermal parameters of the tissue may be used to generate a base model of heat transfer in the tissue based on the finite element method or simpler analytical relations. The inputs to the model may then be further refined using information obtained from the depth-resolved optical data collected from the LCI system. The outputs of the thermal model may be used to calculate a required treatment time in thicker samples where the LCI M-scans do not offer sufficient depth information. For example, to ensure direct transmurality, the thermal model parameters can be used to optimize tissue heating close to sensitive structures, as well as provide an initial estimation of the lateral extension of the formed lesion. These model outputs may be presented to the user (e.g., on a display) or used to directly control RF energy delivery. A combination of LCI information, the computational model, and other relevant information such as the temperature of the tip of the catheter or electro-tissue impedance may be used to predict the temperature distribution in the tissue during ablation and understand the kinetics of the lesion growth.

In an embodiment, two phases are distinguished when using the computational model along with the collected information: a phase where denaturation occurs within the axial penetration depth of the LCI radiation, and a phase where denaturation occurs beyond the axial penetration limit. During the first stage, the temporal evolution of the isothermal line at which collagen birefringence is lost may be monitored along with the temperature of the tip of the catheter. In an embodiment, a processing device coupled to the catheter takes advantage of this information to estimate parameters involved in heat transfer, such as thermal diffusivity, as well as to characterize the effects of irrigation, among others. Once these parameters have been defined, computational models may be used to predict the evolution of tissue ablation beyond the axial penetration limit of the LCI radiation. The information regarding impedance may also be correlated with the previously collected data.

The thermal model of the sample may also be enhanced via structural information regarding the sample. For example, such information can be obtained from pre-operatory magnetic resonance imaging (MRI) or computerized tomography (CT) scans and, when appropriately combined with navigation information, can provide information about wall thickness, shape, and tissue composition in the vicinity of the catheter's distal part.

FIG. 10 illustrates an example method 1000 for performing RF ablation while collecting LCI data, according to an embodiment. Method 1000 may be performed by various components of catheter 100 in conjunction with processing device 108.

At block 1002, a portion of a sample is ablated. The ablation may be due to the application of RF energy by an electrode at the distal end of a catheter, or via other ablation methods such as laser ablation. The sample portion may be, for example, a portion of an atrial wall being ablated to help correct a cardiac arrhythmia.

At block 1004, LCI optical data of the sample is collected while the ablation is occurring. The LCI optical data may include data regarding the portion being ablated and/or portions of the sample not currently being ablated. The collection of the LCI optical data may involve transmitting one or more beams of exposure radiation via corresponding openings arranged at a distal end of the catheter and receiving one or more beams of scattered or reflected radiation from the sample.

At block 1006, depth-resolved optical data is generated based on the beams of radiation received from the sample. For example, a detector may generate an electrical signal based on the received beams of radiation. The generated electrical signal may then be received by a processing device for further analysis and signal processing to perform certain actions and/or generate models based on the depth-resolved optical data. For example, the depth-resolved optical data may be used to determine a degree of ablation for the sample portion being ablated.

At block 1008, a model of heat dissipation of the sample is provided based on the depth-resolved optical data. The thermal model may be either generated or updated based on the depth-resolved optical data, such as the data collected from various M-scans. General thermal properties of the tissue sample, including heat capacity and heat diffusivity, together with other heat transfer effects derived from the thermal model, such as convection close to the surface, may be used to further compute relevant clinical parameters, such as depth and width of the created lesion, according to an embodiment. The thermal model may also be generated based on other collected data beyond the depth-resolved optical data. For example, the temperature at the distal end of the catheter and/or impedance measured at the distal end of the catheter may be collected and used when generating the thermal model. In an embodiment, the thermal model may be used to monitor the ablation process of tissue beyond the penetration range of the LCI radiation. In another example, the model of heat dissipation is used to avoid delivering too much RF energy that may result in atrial wall perforation, thus translating into serious complications for the patient during the procedure.

Additionally, the thermal model may be presented to a user or used to determine whether the user should be alerted in some way. For example, while the ablation procedure is occurring, if the temperature of the ablated region rises above a given threshold as determined by the thermal model, a warning signal may be transmitted to the user. Examples of warning signals include sounding an audio warning, activating a light, or blinking a light. Tactile warnings may be issues as well, such as a slight vibration in the portion of the catheter system being manually handled by the user. In another example, while the ablation procedure is occurring, if the temperature of a portion of the sample near the portion being ablated rises above a given threshold as determined by the thermal model, a warning signal may be transmitted to the user. Alternatively, the ablation procedure may be automatically controlled based on outputs from the thermal model.

In another embodiment, the thermal model is associated with an adaptive/predictive controller to ensure safe RF energy delivery. An adaptive controller may be used to directly control the parameters of the RF energy used for ablation based on the thermal model. In another embodiment, model predictive control, neural networks, or genetic algorithms may be used to minimize a cost function defined in terms of patient safety and accurate energy delivery.

Catheter Navigation

Depth-resolved optical data generated from the LCI system may also be used to aid in the navigation of the catheter to an ablation site, according to an embodiment. In one example, data collection may occur by switching between available view ports at the distal end of a catheter in a predefined or random way. In another embodiment, the system may simultaneously monitor signals from different view ports at the distal end of the catheter. According to an embodiment, while the catheter is being navigated through a cardiac chamber, a processing device may be configured to use the optical data to monitor for close-vicinity or contact with tissue in one or more of the optical view ports. A significant change in the amplitude of the LCI scans is observable between blood, saline solution, and tissues to be ablated (like the different layers of the atrial wall). Accordingly, the processing device may be configured to characterize whether the sample being imaged from a given view port is blood, saline, or tissue. The effective absorption and scattering coefficient, which can be calculated from the depth-resolved optical data, will vary between blood, saline, and tissue. For example, at a wavelength of 1.3 µm, the coefficient is about 8-10 mm$^{-1}$ in the endocardial wall, about 15-20 mm$^{-1}$ in blood, and it can be considered negligible in saline solutions. The endocardial surface of the atrial wall will additionally produce a reflection peak, followed by a rotation in the polarization signal. This characteristic signal may be used to evaluate tissue contact and distance to the atrial wall from any given view port at the distal end of the catheter. Scans acquired sequentially for the same view port may be compared over time. In an embodiment, this information may be used to help navigate the catheter by determining a distance between the distal end of the catheter and any perceived tissue.

Furthermore, the processing device may be configured to validate the assumption of continuous contact and stationary position relative to the tissue to be ablated during the ablation procedure. In an embodiment, the validation is performed by checking for abrupt variations that may appear in the LCI signals and the polarization information, and by monitoring a distance to the first reflection typically appearing at the surface of the tissue wall. If slippage or loss of contact during ablation is detected, a notification for the user may be produced. Alternatively, a feedback control system may be implemented to stabilize the catheter during the ablation procedure.

In an embodiment, the processing device uses two sources of information in order to evaluate tissue contact during the navigation phase, but other parameters resulting from the analysis of the LCI signals can be envisioned, including those extracted using neural networks, wavelet analysis, or others known to those skilled in the art. For example, the processing device may use LCI signal information as well as pressure sensor data (or data collected from an impedance sensor) to evaluate tissue contact. Given the fast line acquisition rate that is possible (several kilohertz), averaging, filtering, or other forms of signal combination can be used to increase signal/image quality. Additionally, the acquired LCI signals may be accumulated to form an M-scan and this information presented for the active view port(s).

FIG. 11 illustrates another example method 1100 for navigating a catheter while collecting LCI data, according to an embodiment. Method 1100 may be performed by various components of catheter 100 in conjunction with processing device 108.

At block 1102, LCI optical data of a sample around the catheter is collected. The sample may include blood, saline, and tissue of an atrial wall as the catheter is navigated through the cardiac chamber. The LCI optical data may include data regarding a portion of the sample to be ablated and/or portions of the sample not to be ablated. The collection of the LCI optical data may involve transmitting one or more beams of exposure radiation via corresponding openings arranged at a distal end of the catheter and receiving one or more beams of scattered or reflected radiation from the sample.

At block 1104, depth-resolved optical data is generated based on the beams of radiation received from the sample. For example, a detector may generate an electrical signal based on the received beams of radiation. The generated electrical signal may then be received by a processing device for further analysis and signal processing to perform certain actions and/or generate models based on the depth-resolved optical data.

At block 1106, the depth-resolved optical data is used to characterize the sample. For example, one or more parameters of the depth-resolved optical data may be compared to determine whether the sample is blood, saline, or tissue. In another example, the electrical impedance of the sample may be calculated by using a bipolar injection of alternating current at a different frequency from that used for ablation. In an embodiment, a processing device is configured to execute software to analyze the depth-resolved optical data. A determination of the sample type may be presented to a user of the catheter, used to generate a map or image of the area surrounding the catheter, or used to directly aid in the navigation of the catheter. For example, the processing device may provide data about tissue type, as extracted from the depth-resolved optical data, to a navigation system configured to move the catheter through the body of a patient. Information about tissue type and ablation results may be displayed on an anatomical map of the tissue to be ablated. This data may be useful in ensuring lesion continuity at the end of, or during, a procedure.

At block 1108, a determination is made regarding whether the sample is tissue or not. If the sample currently being analyzed is not tissue, method 1100 repeats at either block 1102 or block 1104. When further LCI data around the catheter needs to be gathered, method 1100 repeats at block 1102. Alternatively, method 1100 may repeat at block 1104 so that depth-resolved optical data may be generated and analyzed from a different portion of the already-collected LCI data. For example, further LCI data is collected from the area surrounding the catheter (block 1102) only after all of the currently collected LCI data has been analyzed (block 1104). If the sample is determined to be tissue, method 1000 proceeds to block 1110.

At block 1110, a distance between the tissue and the distal end of the catheter is determined. This determination may be made via a processing device configured to analyze the depth-resolved optical data and calculate an approximation of the distance between the tissue and the distal end of the catheter. For example, a time-of-flight of the light reflected from a surface of the tissue may be extracted from the depth-resolved optical data and used to determine distance. The distance information generated by the processing device may be presented to the user to aid in navigation, or used to automatically control the movement of the catheter.

Optical Coherence Tomography Imaging

In an embodiment, the processing device provides an additional mode in which the information derived from the depth-resolved optical data is used to determine the 3D spatial position and orientation of the catheter tip. The catheter may be swept over a portion of the sample while LCI data is being collected, to provide spatially-resolved data for 3D modeling. The processing device may be configured to accumulate the depth-resolved optical data associated with one or more LCI scans from the active optical viewport, and arrange the data according to a spatial position of the catheter into one or more Optical Coherence Tomography (OCT) images or 3D reconstructions. In an embodiment, the processing device adapts a scanning rate of the LCI system and the function of the optical multiplexer to match the variable lateral sweeping speed of the catheter. The OCT images may be purely structural or may include information about refractivity of the tissue (e.g., birefringence). These images may be useful in ensuring lesion quality, continuity, and transmurality at the end of or during a procedure.

FIG. 12 illustrates another example method 1200 for collecting OCT images of a sample around a catheter. Method 1200 may be performed by various components of catheter 100 in conjunction with processing device 108.

At block 1202, LCI optical data of a sample around the catheter is collected. The sample may include blood, saline, and tissue of the atrial wall as the catheter is navigated through the cardiac chamber. The LCI optical data may include data regarding a portion of the sample to be ablated and/or portions of the sample not to be ablated. The collection of the LCI optical data may involve transmitting one or more beams of exposure radiation via corresponding openings arranged at a distal end of the catheter and receiving one or more beams of scattered or reflected radiation from the sample.

At block 1204, the catheter is swept over a portion of the sample. According to an embodiment, the sweeping occurs while the LCI data is being collected. Alternatively, the catheter itself may be substantially stationary while scanning elements located at the view ports of the catheter cause exposure light exiting from the view ports to be swept in a given direction.

At block 1206, depth-resolved optical data is generated based on the beams of radiation received from the sample. For example, a detector may generate an electrical signal based on the received beams of radiation. The generated electrical signal may then be received by a processing device for further analysis and signal processing to perform certain actions and/or generate models based on the depth-resolved optical data.

At block 1208, an OCT image of the portion of the sample swept over by the catheter is generated based on the depth-resolved optical data. A processing device may be configured to generate a 3-D model of the sample portion by combining the depth-resolved optical data taken during the sweep. The OCT image may be presented to a user, for example, as an image on a display device, to provide the user with a better visual representation of the sample around the catheter. The processing device may also be configured to determine relevant parameters about the sample from the OCT data, such as, for example, a refractivity coefficient associated with birefringence.

Example Computer System Embodiment

Various image processing methods and other embodiments described thus far can be implemented, for example, using one or more well-known computer systems, such as computer system 1300 shown in FIG. 13. In an embodiment, computer system 1300 may be an example of processing device 108 illustrated in FIG. 1.

Computer system 1300 includes one or more processors (also called central processing units, or CPUs), such as a processor 1304. Processor 1304 is connected to a communication infrastructure or bus 1306. In one embodiment, processor 1304 represents a field programmable gate array (FPGA). In another example, processor 1304 is a digital signal processor (DSP).

One or more processors 1304 may each be a graphics processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

Computer system 1300 also includes user input/output device(s) 1303, such as monitors, keyboards, pointing devices, etc., which communicate with communication infrastructure 1306 through user input/output interface(s) 1302.

Computer system 1300 also includes a main or primary memory 1308, such as random access memory (RAM). Main memory 1308 may include one or more levels of cache. Main memory 1308 has stored therein control logic (i.e., computer software) and/or data.

Computer system 1300 may also include one or more secondary storage devices or memory 1310. Secondary memory 1310 may include, for example, a hard disk drive 1312 and/or a removable storage device or drive 1314. Removable storage drive 1314 may be a floppy disk drive, a magnetic tape drive, a compact disc drive, an optical storage device, tape backup device, and/or any other storage device/drive.

Removable storage drive 1314 may interact with a removable storage unit 1318. Removable storage unit 1318 includes a computer usable or readable storage device having stored thereon computer software (control logic) and/or data. Removable storage unit 1318 may be a floppy disk, magnetic tape, compact disc, Digital Versatile Disc (DVD), optical storage disk, and/any other computer data storage device. Removable storage drive 1314 reads from and/or writes to removable storage unit 1318 in a well-known manner.

Secondary memory 1310 may include other means, instrumentalities, or approaches for allowing computer programs and/or other instructions and/or data to be accessed by computer system 1300. Such means, instrumentalities or other approaches may include, for example, a removable storage unit 1322 and an interface 1320. Examples of the removable storage unit 1322 and the interface 1320 may include a program cartridge and cartridge interface (such as that found in video game devices), a removable memory chip (such as an EPROM or PROM) and associated socket, a memory stick and universal serial bus (USB) port, a memory card and associated memory card slot, and/or any other removable storage unit and associated interface.

Computer system 1300 may further include a communication or network interface 1324. Communication interface 1324 enables computer system 1300 to communicate and interact with any combination of remote devices, remote networks, remote entities, etc. (individually and collectively referenced by reference number 1328). For example, communication interface 1324 may allow computer system 1300 to communicate with remote devices 1328 over communications path 1326, which may be wired and/or wireless, and which may include any combination of local area networks (LANs), wide area networks (WANs), the Internet, etc. Control logic and/or data may be transmitted to and from computer system 1300 via communication path 1326.

In an embodiment, a tangible apparatus or article of manufacture comprising a tangible computer useable or readable medium having control logic (software) stored thereon is also referred to herein as a computer program product or program storage device. This includes, but is not limited to, computer system 1300, main memory 1308, secondary memory 1310, and removable storage units 1318 and 1322, as well as tangible articles of manufacture embodying any combination of the foregoing. Such control logic, when executed by one or more data processing devices (such as computer system 1300), causes such data processing devices to operate as described herein.

Based on the teachings contained in this disclosure, it will be apparent to persons skilled in the relevant art(s) how to make and use the invention using data processing devices, computer systems and/or computer architectures other than that shown in FIG. 13. In particular, embodiments may operate with software, hardware, and/or operating system implementations other than those described herein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method, comprising:
    ablating a portion of a sample using RF energy from one or more electrodes on a distal end of a catheter;
    transmitting exposure radiation along a plurality of scan lines in different directions via a corresponding plurality of view ports arranged at the distal end of the catheter, wherein each scan line intersects different locations within the portion of the sample and a phase of radiation transmitted via a first viewport of the plurality of viewports is different from a phase of radiation transmitted via a second viewport of the plurality of viewports;

receiving scattered or reflected radiation along the plurality of scan lines from different depths within the portion of the sample at the corresponding plurality of view ports;

guiding the received scattered or reflected radiation using optical elements, each optical element being associated with a respective view port of the plurality of view ports;

generating depth-resolved optical data corresponding to the plurality of scan lines based on the received scattered or reflected radiation from the different depths within the portion of the sample; and determining a model of heat distribution at least in the portion of the sample from the depth-resolved optical data.

2. The method of claim 1, further comprising determining, based on the depth-resolved optical data, a degree of ablation for the portion of the sample.

3. The method of claim 1, further comprising, while the RF energy is being generated, transmitting a warning signal to a user of the catheter when the model of thermal properties indicates that a temperature of the portion of the sample increases above a given threshold.

4. The method of claim 1, further comprising, while the RF energy is being generated, transmitting a warning signal to a user of the catheter when the model of thermal properties indicates that a temperature of another portion of the sample increases above a given threshold.

5. The method of claim 1, further comprising:
using the generated depth-resolved optical data to determine when the ablation of the portion of the sample is complete; and
transmitting a signal to a user of the catheter when the ablation of the portion of the sample is complete.

6. The method of claim 1, wherein the generating depth-resolved optical data comprises generating data based on a birefringence of the sample.

7. A catheter, comprising:
a distal section comprising:
one or more electrodes configured to apply RF energy to a portion of a sample in contact with the one or more electrodes, such that the portion of the sample is ablated;
a plurality of view ports configured to:
transmit exposure radiation along a corresponding plurality of scan lines in different directions, wherein each scan line intersects different locations within the portion of the sample and a phase of radiation transmitted via a first viewport of the plurality of viewports is different from a phase of radiation transmitted via a second viewport of the plurality of viewports, and
receive radiation that has been reflected or scattered along the plurality of scan lines from different depths within the portion of the sample; and
a plurality of optical elements configured to guide at least the received radiation, wherein each of the plurality of optical elements corresponds with each of the plurality of view ports;
a proximal section comprising:
an optical source configured to generate a source beam of radiation; and
a detector configured to generate depth-resolved optical data associated with the reflected or scattered radiation from the different depths within the sample;
a sheath coupled between the proximal section and the distal section; and
a processing device configured to update a model of thermal properties of the sample from the depth-resolved optical data.

8. The catheter of claim 7, further comprising a multiplexer configured to generate the exposure radiation from a source beam of radiation.

9. The catheter of claim 7, wherein the plurality of view ports are arranged around an outer surface of the distal section.

10. The catheter of claim 7, wherein the plurality of optical elements are further configured to transmit each of one or more beams of the exposure radiation through a corresponding view port of the plurality of view ports.

11. The catheter of claim 7, wherein the processing device is further configured to:
receive the depth-resolved optical data, and
generate an image of the sample based on the depth-resolved optical data.

12. The catheter of claim 11, wherein the depth-resolved optical data includes data associated with a birefringence of the sample, and wherein the image of the sample is generated based on a difference between a first birefringence associated with the portion of the sample ablated by the RF energy, and a second birefringence associated with at least one other non-ablated portion of the sample.

* * * * *